(12) United States Patent
Yang et al.

(10) Patent No.: US 9,533,965 B2
(45) Date of Patent: Jan. 3, 2017

(54) 2-ARYLBENZOFURAN-7-FORMAMIDE COMPOUNDS, PREPARATION METHOD AND USE THEREOF

(71) Applicants: SHANGHAI INSTITUTE OF MATERIA MEDICA, CHINESE ACADEMY OF SCIENCES, Shanghai (CN); CISEN PHARMACEUTICAL CO., LTD., Jining (CN)

(72) Inventors: Chunhao Yang, Shanghai (CN); Zehong Miao, Shanghai (CN); Jian Ding, Shanghai (CN); Meng Wang, Shanghai (CN); Jinxue He, Shanghai (CN); Cun Tan, Shanghai (CN); Yi Chen, Shanghai (CN)

(73) Assignees: SHANGHAI INSTITUTE OF MATERIA MEDICA, CHINESE ACADEMY OF SCIENCES, Shanghai (CN); CISEN PHARMACEUTICAL CO., LTD., Jining (CN)

( * ) Notice: Subject to any disclaimer, the term of this patent is extended or adjusted under 35 U.S.C. 154(b) by 84 days.

(21) Appl. No.: 14/375,742

(22) PCT Filed: Jan. 14, 2013

(86) PCT No.: PCT/CN2013/070410
§ 371 (c)(1),
(2) Date: Jul. 30, 2014

(87) PCT Pub. No.: WO2013/117120
PCT Pub. Date: Aug. 15, 2013

(65) Prior Publication Data
US 2015/0018542 A1    Jan. 15, 2015

(30) Foreign Application Priority Data

Feb. 9, 2012    (CN) .......................... 2012 1 0028895

(51) Int. Cl.
| | |
|---|---|
| *A61K 31/343* | (2006.01) |
| *A61K 31/4025* | (2006.01) |
| *A61K 31/443* | (2006.01) |
| *A61K 31/496* | (2006.01) |
| *A61K 31/501* | (2006.01) |
| *A61K 31/5355* | (2006.01) |
| *A61K 31/541* | (2006.01) |
| *A61K 31/551* | (2006.01) |
| *C07D 307/79* | (2006.01) |
| *C07D 405/04* | (2006.01) |
| *C07D 405/10* | (2006.01) |

(Continued)

(52) U.S. Cl.
CPC ............. *C07D 307/81* (2013.01); *C07C 67/08* (2013.01); *C07C 67/307* (2013.01); *C07D 405/04* (2013.01); *C07D 405/12* (2013.01); *C07D 407/12* (2013.01)

(58) Field of Classification Search
CPC   A61K 31/343; A61K 31/4025; A61K 31/443; A61K 31/496; A61K 31/501; A61K 31/5355; A61K 31/541; A61K 31/551; C07D 307/79; C07D 405/04;C07D 405/10; C07D 405/14; C07D 413/10; C07D 413/14; C07D 417/10; C07D 417/14
USPC ........ 514/218, 228.2, 233.5, 252.01, 254.11, 514/318, 320, 422, 469; 540/575; 544/62, 544/153, 238, 376; 546/196; 548/525; 549/467
See application file for complete search history.

(56) References Cited

FOREIGN PATENT DOCUMENTS

| CN | 102627620 A | 8/2012 |
|---|---|---|
| EP | 0306226 A2 | 3/1989 |

(Continued)

OTHER PUBLICATIONS

English language translation of CN 102627620, 2012.*

(Continued)

*Primary Examiner* — Brenda Coleman
(74) *Attorney, Agent, or Firm* — Mintz, Levin, Cohn, Ferris, Glovsky and Popeo, P.C.

(57) ABSTRACT

Provided in the present invention are a 2-arylbenzofuran-7-formamide compound as shown in general formula I or a pharmacologically or physiologically acceptable salt thereof, a preparation method thereof and use thereof in preparing anti-tumour drugs, wherein $R_1$ and $R_2$ are each independently hydrogen, straight or branched chained $C_1$-$C_4$ alkyl, $C_3$-$C_4$ cycloalkyl or saturated 5- or 6-membered heterocyclyl containing oxygen or nitrogen; or $R_1$ and $R_2$ together with N form an unsubstituted or substituted saturated 5- or 6-membered heterocyclyl containing at least one heteroatom, wherein the heteroatom is O, N and S, the substituent is a methyl on N; $R_3$ is a hydrogen atom or a chlorine atom; $R_4$ is a hydrogen atom or a fluorine atom; X is CH, CF or N; and Y is CH, CF or N.

8 Claims, No Drawings

(51) Int. Cl.
   *C07D 405/14* (2006.01)
   *C07D 413/10* (2006.01)
   *C07D 413/14* (2006.01)
   *C07D 417/10* (2006.01)
   *C07D 417/14* (2006.01)
   *C07D 307/81* (2006.01)
   *C07D 405/12* (2006.01)
   *C07C 67/08* (2006.01)
   *C07C 67/307* (2006.01)
   *C07D 407/12* (2006.01)

(56) References Cited

FOREIGN PATENT DOCUMENTS

| | | | |
|---|---|---|---|
| WO | 2005/047275 | A1 | 3/2005 |
| WO | 2008/098978 | A2 | 8/2008 |
| WO | 2008/098978 | A3 | 8/2008 |
| WO | 2009/009417 | A2 | 1/2009 |
| WO | 2009/124968 | A1 | 10/2009 |
| WO | 2011/022679 | A2 | 2/2011 |
| WO | 2011/022679 | A3 | 2/2011 |
| WO | 2011/055115 | A1 | 5/2011 |

OTHER PUBLICATIONS

International Search Report (English translation) corresponding to PCT/CN2013/070410 mailed Apr. 25, 2013 (3 pages).
Bryant, Helen E. et al., "Specific killing of BRCA2-deficient tumours with inhibitors of poly(ADP-ribose) polymerase," *Nature* (Apr. 14, 2005) 434:913-916.
Chen, Cheng-yi et al., "Synthesis of Benzo[*b*]furans via CuI-Catalyzed Ring Closure," *J. Org. Chem.* (2005) 70(17):6964-6967.
Emirdag-Ozturk, Safiye et al., "Synthesis of egonol derivatives and their antimicrobial activities," *Bioorg. Med. Chem.* (2011) 19:1179-1188.
Farmer, Hannah et al., "Targeting the DNA repair defect in *BRCA* mutant cells as a therapeutic strategy," *Nature* (Apr. 14, 2005) 434:917-921.
Ferraris, Dana V., "Evolution of Poly(ADP-ribose) Polymerase-1 (PARP-1) Inhibitors. From Concept to Clinic," *J. Med. Chem.* (2010) 53(12):4561-4584.
Flynn, Bernard L. et al., "One-Pot Synthesis of Benzo[b]furan and Indole Inhibitors of Tubulin Polymerization," *J. Med. Chem.* (2002) 45(12):2670-2673.
Halabalaki, Maria et al., "Three New Arylobenzofurans from *Onobrychis ebenoides* and Evaluation of Their Binding Affinity for the Estrogen Receptor," *J. Nat. Prod.* (2000) 63(12):1672-1674.

He, Jin-xue et al., "Poly(ADP-ribose) polymerase inhibitors as promising cancer therapeutics," *Acta Pharmacoligica Sinica* (2010) 31:1172-1180.
Hoeijmakers, Jan H. J., "Genome maintenance mechanisms for preventing cancer," *Nature* (May 17, 2001) 411:366-374.
Kaelin, Jr., William G., "The Concept of Synthetic Lethality in the Context of Anticancer Therapy," *Nature Reviews/Cancer* (Sep. 2005) 5:689-698.
Lee, Sunkyung et al., "Studies on Benzofuran-7-carboxamides as Poly(ADP-ribose) Polymerase-1 (PARP-1) Inhibitors," *Bull. Korean Chem. Soc.* (2012) 33(4):1147-1153.
Liang, Zhidan et al., "Oxidative Aromatic C—O Bond Formation: Synthesis of 3-Functionalized Benzo[*b*]furans by $FeCl_3$-Mediated Ring Clsoure of α-Aryl Ketones," *Org. Lett.* (2009) 11(21):4978-4981.
Nakatani, Shingo et al., "Design and synthesis of novel metalloproteinase inhibitors," *Bioorg. Med. Chem.* (2006) 14:5402-5422.
Peralta-Leal, Andreina et al., "PARP inhibitors: New partners in the therapy of cancer and inflammatory diseases," *Free Radical Biology & Medicine* (2009) 47:13-26.
Perez Santin, Efren et al., "Highly Potent Naphthofuran-Based Retinoic Acid Receptor Agonists," *ChemMedChem* (2009) 4:780-791.
Rouleau, Michele et al., "PARP inhibition: PARP1 and beyond," *Nature Reviews/Cancer* (Apr. 2010) 10:293-301.
Schreiber, Valerie et al., "Poly(ADP-ribose): novel functions for an old molecule," *Nature Reviews/Molecular Cell Biology* (Jul. 2006) 7:517-528.
Tsai, Ian-Lih et al., "Additional Cytotoxic Neolignans from *Persea obovatifolia*," *Phytochemistry* (1998) 48(8):1371-1375.
Underhill, C. et al., "A review of PARP inhibitors: from bench to bedside," *Annals of Oncology*, (Jul. 19, 2010) doi:10.1093/annonc/mdq322 (12 pages).
Yelamos, Jose et al., "PARP-1 and PARP-2: New players in tumour development," *Am. J. Cancer Res.* (2011) 1(3):328-346.
Zaremba, Tomasz et al., "PARP Inhibitor Development for Systemic Cancer Targeting," *Anti-Cancer Agents in Medicinal Chemistry* (2007) 7(5):515-523.
Ziegert, Robert E. et al., "The Recent Impact of Solid-Phase Synthesis on Medicinally Relevant Benzoannelated Oxygen Heterocycles," *Journal of Combinatorial Chemistry* (2005) 7(2):147-169.
Brenner, J. Chad et al., "Mechanistic Rationale for Inhibition of Poly(ADP-Ribose) Polymerase in ETS Gene Fusion-Positive Prostate Cancer," *Cancer Cell* (May 17, 2011) 19:664-678.
Wang, Li et al., "MK-4827, a PARP-1/-2 inhibitor, strongly enhances response of human lung and breast cancer xenografts to radiation," *Invest New Drugs* ((2012); accepted Nov. 14, 2011); 30:2113-2120.

* cited by examiner

2-ARYLBENZOFURAN-7-FORMAMIDE COMPOUNDS, PREPARATION METHOD AND USE THEREOF

TECHNICAL FIELD

The invention belongs to the field of pharmaceutical chemistry and pharmacotherapy, specially to a 2-arylbenzofuran-7-carboxamide compounds or pharmacologically or physiologically acceptable salts thereof, preparation methods and use thereof in preparing a medicament for treating poly(adenosine diphosphate[ADP]-ribose) polymerase-related diseases such as malignant tumours.

BACKGROUND ART

Poly(adenosine diphosphate[ADP]-ribose) polymerase (PARP) is a nuclear enzyme in most eukaryocytes and the main function thereof is to synthesize poly(ADP-ribose) (PAR) using nicotinamide adenine dinucleotide ($NAD^+$) as its substrate and transfer the synthesized poly(ADP-ribose) to receptor protein, thereby regulating the function of protein (see: Schreiber, V.; Dantzer, F.; Ame, J. C.; de Murcia, G. Poly(ADPribose): novel functions for an old molecule. Nat. Rev. Mol. Cell Biol. 2006, 7, 517-528). At least 16 homologs in PARP family have been found and only six members (PARP1, PARP2, PARP3, PARP4 (VPARP), Tankyrase1 and Tankyrase2, respectively) have poly(ADP-ribose) polymerase function according to stringent structural and functional criteria, while other members in the family may function as mono-ADP-ribosyltransferases (see: Rouleau, M.; Patel, A.; Hendzel, M. J.; Kaufmann, S. H.; Poirier, G. G. PARP inhibition: PARP1 and beyond. Nat. Rev. Cancer 2010, 10, 293-301). Only PARP1 and PARP2 in PARP family can be activated by the breaks of DNA strands, mediate polyADP-ribosylation, and participate in the repair of DNA single-strand breaks through the base-excision repair (BER) pathway. PolyADP-ribosylation causes chromatin depolymerization in the injured site, initiates repair mechanism and accelerates the repair of DNA damage. In that respect, PARP1 and PARP2 play dual roles including detection of DNA damage and signaling transduction during the repairing process. Human PARP1 is a polypeptide with molecular weight of 113 kDa and contains three functional domains. The DNA binding domain (DBD) located at the N-terminal end contains two Zinc fingers recognizing DNA single-strand breaks and double-strand breaks. The automodification domain is located in the middle region, by which PARP1 binds to ADP ribosyl thereby polyADP-ribosylating PARP itself. And the catalytic domain located in the C-terminal end acts as the basis for transferring $NAD^+$ to ADP ribose and is the active structure for the function of PARP1. In contrast, human PARP2 is a polypeptide with molecular weight of 62 kDa. Its DNA binding domain is different from that of PARP1, and accordingly the main function thereof is to recognize the gap due to the deletion of nucleotide in the damaged DNA strand. The catalytic domain located at the C-terminal end of PARP2 is similar to that of PARP1, however, the fine difference in their structures still reflects the difference in their target proteins to be catalyzed. PARP1 and PARP2 play an important role in the repair of DNA damage, genome stability and regulation of cell apoptosis through base excision repair. Therefore, they become one of the most interesting targets in anti-tumour drug research in recent years (see: Yelamos, J.; Farres, Jordi.; Llacuna, L.; Ampurdanes, C.; targeCaballero, J. M. PARP-1 and PARP-2: New players in tumour development. Am. J. Cancer Res. 2011, 1(3), 328-346). Moreover, the important role of PARP in the process such as inflammation, ischemia reperfusion, etc., indicates that PARP also has potential application value in the diseases (such as diabetes, cardiovascular disease, etc.) except for malignant tumours (see: Peralta-Leal, A.; Rodriguez-Vargas, J. M.; Aguilar-Quesada, R.; Rodriguez, M. I.; Linares, J. L.; de Almodovar, M. R.; Oliver, F. J. PARP inhibitors: new partners in the therapy of cancer and inflammatory diseases. Free Radical Biol. Med. 2009, 47, 13-26).

In 2005, it was reported in Nature that PARP1/2 inhibitors used alone have a significantly intibiting effect on breast cancer cells with defective BRCA1/2 (see: Bryant, H. E.; Schultz, N.; Thomas, H. D.; Parker, K. M.; Flower, D.; Lopez, E.; Kyle, S.; Meuth, M.; Curtin, N. J.; Helleday, T. Specific killing of BRCA2-deficient tumours with inhibitors of poly(ADP-ribose) polymerase. Nature 2005, 434, 913-917. And Farmer, H.; McCabe, N.; Lord, C. J.; Tutt, A. N.; Johnson, D. A.; Richardson, T. B.; Santarosa, M.; Dillon, K. J.; Hickson, I.; Knights, C.; Martin, N. M.; Jackson, S. P.; Smith, G. C.; Ashworth, A. Targeting the DNA repair defect in BRCA mutant cells as a therapeutic strategy. Nature 2005, 434, 917-921.), which represented a breakthrough in the research of using PARP1/2 inhibitors alone for anti-tumour treatment. DNA is unstable and can be damaged due to the exposure to harsh environment (such as ultraviolet radiation, ionizing radiation, etc.), byproducts from normal cell metabolism, and breaks in some DNA chemical bonds. For keeping the genome intact and stable, normal human cells need to repair DNA damages caused by various factors for tens of thousands of times every day. Major DNA repair pathways include base excision repair (BER), nucleotide-excision repair (NER), homologous recombination (FIR) and nonhomologous end joining (NHEJ); wherein, BER in which PARP1/2 participates is the uppermost repair pathway for DNA single-strand breaks, while FIR is the uppermost repair pathway for DNA double-strand breaks (see: Hoeijmakers, J. H. Genome maintenance mechanisms for preventing cancer. Nature 2001, 411, 366-74). BRCA1/2 are famous tumour-suppressor genes and key repair factors in HR. Defects in BRCA1/2 will increase the unstability of genome and cause the occurrence of malignant tumour. For such cells, DNA double-strand breaks can not be repaired by HR and breaks will finally lead to the death of cells. Inhibiting PARP1/2 in BRCA1/2-deficient tumor cells leads to increase the accumulation of DNA single-strand breaks; when colliding with the replication forks in progression, DNA single-strand breaks are converted to lethal double-strand breaks which ultimately results in cell killing. The phenomenon that inhibition of PARP1/2 together with defects of BRCA1/2 kills cells is so called as synthetic lethality. The use of the synthetic lethality phenomenon provides a new strategy for treating malignant tumours, thereby opening a new era of PARP1/2 inhibitors for research and development of high selectivity anti-tumour drugs (see: Kaelin, W. G., Jr. The concept of synthetic lethality in the context of anticancer therapy. Nat. Rev. Cancer 2005, 5, 689-698; He J X, Yang C H, Miao Z H. PARP inhibitors as promising cancer therapeutics. Acta Pharmacol. Sin. 2010, 31, 1172-1180).

The first generation of PARP1/2 inhibitors was emerged thirty years ago, and most of them are nicotinamide analogues, but such inhibitors lack selectivity and effectiveness. The second generation of PARP1/2 inhibitors was developed in 1990s and clear structure-activity relationships were established; therefore, PARP1/2 inhibitors have more clear structure features. The structure features include an electronrich aromatic ring; a carboxamide group at least containing one free hydrogen for forming hydrogen bonding; and one non-cleavable chemical bond at the position corresponding to the 3-position pharmacophore of the carboxamide, etc. (see: Zaremba, T.; Curtin, N. J. PARP inhibitor development for systemic cancer targeting. Anti-Cancer Agents Med. Chem. 2007, 7, 515-523). At present at least seven PARP1/2 inhibitors as new anti-tumour drugs have entered clinical trials (see: C. Toulmondel, U. M.; Bonnefoi, H. A review of PARP inhibitors: from bench to bedside. Annals of Oncology 2011, 22(2), 268-79; Ferraris, D. V. Evolution of Poly (ADP-ribose) Polymerase-1 (PARP-1) Inhibitors. From Concept to Clinic. J. Med. Chem. 2010, 53, 4561-4584; He J X, Yang C H, Miao Z H. PARP inhibitors as promising cancer therapeutics. Acta Pharmacol. Sin. 2010, 31, 1172-1180). However, these inhibitors still have many disadvantages, such as relatively low oral bioavailability, lack of selectivity for PARP subtypes except PARP1/2 and so on.

As well known, 2-arylbenzofuran compounds widely exist in natural products. Due to their good bioactivities and potential pharmaceutical values, the researchers always pay a close attention to them. On the one hand, the scientists studying natural products continuously extract and isolate novel 2-arylbenzofuran compounds from natural products, and investigate and develop biological activities thereof (see: Halabalaki, M.; Aligiannis, N.; Papoutsi, Z.; Mitakou, S.; Moutsatsou, P.; Sekeris, C.; Skaltsounis, A.-L. Three New Arylobenzofurans from Onobrychis ebenoides and Evaluation of Their Binding Affinity for the Estrogen Receptor. J. Nat. Prod. 2000, 63, 1672-1674; and Tsai, I. L.; Hsieh, C.-F.; Duh, C.-Y. Additional Cytotoxic Neoligants From Perseaobovatifolia. Phytochemistry 1998, 48, 1371-1375); on the other hand, great efforts have been made by the chemists to develop and optimize a series of methods for constructing 2-arylbenzofuran compounds (see: Ziegert, R. E.; Torang, J. Knepper, K.; Brase, S. The Recent Impact of Solid-Phase Synthesis on Medicinally Relevant Benzoannelated Oxygen Heterocycles. J. Comb. Chem. 2005, 7, 147-169. Chen, C. Y.; Dormer, P. G. Synthesis of Benzo[b] furans via CuI-Catalyzed Ring Closure. J. Org. Chem. 2005, 70, 6964-6967. And Liang, Z. D.; Hou, W. Z.; Du, Y. F.; Zhang, Y. L.; Pan, Y.; Mao, D.; Zhao, K. Oxidative Aromatic C—O Bond Formation: Synthesis of 3-Functionalized Benzo[b]furans by FeCl$_3$-Mediated Ring Closure of α-Aryl Ketones. Org. Lett. 2009, 21, 4978-4981, etc.). Various activities have been exhibited by reported 2-arylbenzofuran compounds, such as retinoic acid receptor (RAP) agonists (see: Santin, E. P.; Khanwalkar H.; Voegel, J.; Collette, P.; Mauvais, P.; Gronemeyer, H.; A. R. de Lera. Highly Potent Naphthofuran-Based Retinoic Acid Receptor Agonists. ChemMedChem. 2009, 4, 780-791), tubulin polymerization inhibitors (see: Flynn, B. L.; Hamel E.; Jung, M. K. One-Pot Synthesis of Benzo[b]furan and Indole Inhibitors of Tubulin Polymerization. J. Med. Chem. 2002, 45, 2670-2673), metalloproteinase inhibitors (see: Nakatani, S.; Ikura, M.; Yamamoto, S.; Nishita, Y.; Itadani, S.; Habashita, H.; Sugiura, T.; Ogawa, K.; Ohno, H.; Takahashi, K.; Nakai, H.; Toda, M. Design and synthesis of novel metalloproteinase inhibitors. Bioorg. Med. Chem. 2006, 14, 5402-5422), and antimicrobial agents (see: Emirdag-Ozturk, S.; Karayildirim, T.; Anil, H. Synthesis of egonol derivatives and their antimicrobial activities. Bioorg. Med. Chem. 2011, 18, 1179-1188). Due to the good biological activities and potentially huge medical values, some compounds have been patented, for example, a use for treating diseases relating to prostaglandin E2 receptor (WO 2008/098978), a use for treating diseases relating to cannabinoid receptor (WO 2011/022679), a use for treating diseases relating to estrogen receptor (WO 2009/124968), a use for preventing bacterial and fungal infection (WO 2005/047275), and a use for treating bladder muscle reflex contraction disease (EP 0306226A2). The above reported 2-arylbenzofuran compounds were not covered for the use as PARP1/2 inhibitors thereof according to the present invention.

Based on above reasons, the inventors designed and synthesized novel 2-arylbenzofuran-7-carboxamide compounds as PARP1/2 inhititors with high selectivity. The compounds according to the present invention have clear structure-activity relationships, and some compounds such as compound 5b have high selectivity to PARP1/2 and excellent bioavailability (After 10 mg/kg of 5b was administrated to rats by gavage, the absolute bioavailability was 58.9%, while the oral bioavailability of rats for the compound AZD2281 during phase II clinical trials was only 11.1%). Such a novel PARP1/2 inhibitor is of promise to become a novel anti-tumour medicament.

SUMMARY OF THE INVENTION

The object of the present invention is to provide 2-arylbenzofuran-7-carboxamide compounds as shown in general formula I or pharmacologically or physiologically acceptable salts thereof,

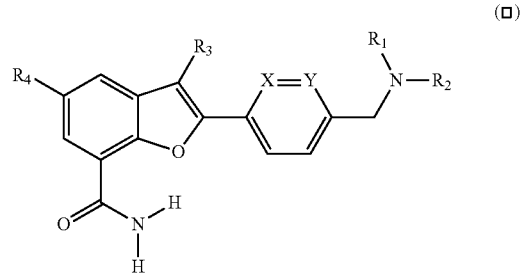

wherein, each of $R_1$ and $R_2$ is independently H, a straight or branched $C_1$-$C_4$ alkyl, a $C_3$-$C_4$ cycloalkyl or a saturated 5- or 6-membered heterocyclic group containing O or N;

or $R_1$ and $R_2$ together with N form an unsubstituted or substituted saturated 5- or 6-membered heterocyclic group containing at least one heteroatom, wherein the heteroatom is O, N and S, the substituent is a methyl on N;

$R_3$ is a hydrogen atom or a chlorine atom;

$R_4$ is a hydrogen atom or a fluorine atom;

X is CH, CF or N; and

Y is CH, CF or N.

Preferably, $R_1$ is H, a methyl, an ethyl, an isopropyl, a cyclopropyl, a piperidin-4-yl or (R)tetrahydrofuran-3-yl;

$R_2$ is H, a methyl, an ethyl, an isopropyl, a cyclopropyl, a piperidin-4-yl or (R)tetrahydrofuran-3-yl;

or $R_1$ and $R_2$ together with N form an unsubstituted or substituted morpholinyl, piperazinyl, homopiperazinyl, thiomorpholinyl, piperidinyl or pyrrolidinyl, wherein the substituent is a methyl on N;

$R_3$ is a hydrogen atom;

$R_4$ is a fluorine atom;

X is CH, CF or N; and

Y is CH, CF or N.

More preferably, $R_1$ is H or a methyl;

$R_2$ is a methyl, an isopropyl, a cyclopropyl, a piperidin-4-yl or (R)tetrahydrofuran-3-yl;

or $R_1$ and $R_2$ together with N form an unsubstituted or substituted morpholinyl, piperazinyl, homopiperazinyl, thiomorpholinyl, piperidinyl or pyrrolidinyl, wherein the substituent is a methyl on N;

$R_3$ is a hydrogen atom;

$R_4$ is a fluorine atom;

X is CH, CF or N; and

Y is CH, CF or N.

The invention provides the most preferable compound as shown in table 1:

| No. | structural formula | $R_1$ | $R_2$ | X | Y | $R_3$ | $R_4$ |
|---|---|---|---|---|---|---|---|
| 5a | | $CH_3$ | $CH_3$ | CH | CH | H | F |
| 5b | | H | $CH_3$ | CH | CH | H | F |
| 7a | | $CH_3$ | $CH_3$ | CH | CH | Cl | F |
| 5c | | H | $CH_3$ | CH | N | H | F |
| 5d | | H | $CH_3$ | N | CH | H | F |

| No. | structural formula | R₁ | R₂ | X | Y | R₃ | R₄ |
|---|---|---|---|---|---|---|---|
| 5e | (structure) | H | CH₃ | CH | CF | H | F |
| 5f | (structure) | \[R₁–N–R₂ = pyrrolidine\] | | CH | CH | H | F |
| 5g | (structure) | \[R₁–N–R₂ = N-methylpiperazine\] | | CH | CH | H | F |
| 5h | (structure) | \[R₁–N–R₂ = piperidine\] | | CH | CH | H | F |
| 5i | (structure) | \[R₁–N–R₂ = N-methyl-homopiperazine\] | | CH | CH | H | F |
| 5j | (structure) | \[R₁–N–R₂ = morpholine\] | | CH | CH | H | F |
| 5k | (structure) | \[R₁–N–R₂ = thiomorpholine\] | | CH | CH | H | F |

| No. | structural formula | R₁ | R₂ | X | Y | R₃ | R₄ |
|---|---|---|---|---|---|---|---|
| 5l | (structure) | H | (4-piperidinyl) | CH | CH | H | F |
| 5m | (structure) | H | (3-tetrahydrofuranyl) | CH | CH | H | F |
| 5n | (structure) | H | (cyclopropyl) | CH | CH | H | F |
| 5o | (structure) | H | (isopropyl) | CH | CH | H | F |
| 5p | (structure) | H | CH₃ | CF | CH | H | F. |

Preferably, the pharmacologically or physiologically acceptable salt is a hydrochloride.

Another object of the present invention is to provide a method for the preparation of the compounds of general formula I, the synthesis route of which is shown as scheme 1:

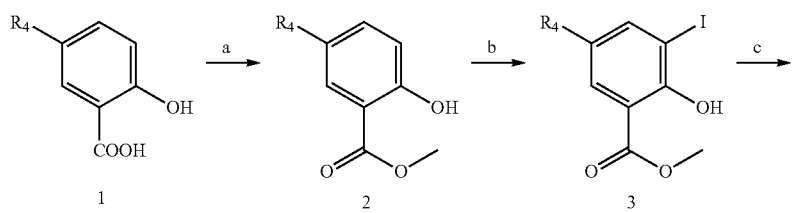

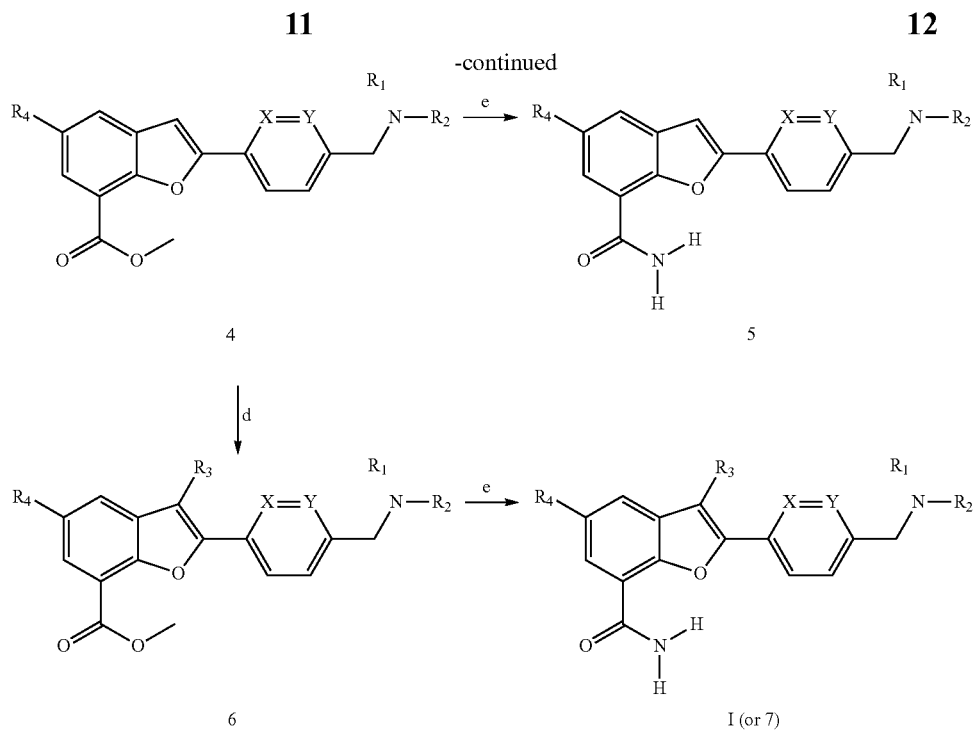

a) a substituted salicylic acid substituted on 5-position is subjected to an esterification reaction to form compound 2;

b) compound 2 is subjected to an iodination reaction to form compound 3;

c) compound 3 and a substituted aromatic alkyne 8 are subjected to a Sonogashira reaction and then cyclization to form compound 4;

d) compound 4 is subjected to a halogenation reaction to form compound 6;

e) compound 4 or 6 is subjected to an ammonolysis reaction to form compound 5 or I (or 7), respectively;

the condition for step a) is that: reflux is performed with methanol as solvent in the presence of catalytic amount of acid such as sulfuric acid;

the condition for step b) is that: N,N-dimethyl formamide is used as solvent, and compound 2 and N-iodosuccinimide are stirred at room temperature under nitrogen until the completion of the reaction is determined by thin layer chromatography;

the condition for step c) is that: N,N-dimethyl formamide is used as solvent, bis(triphenylphosphine)palladium(II) dichloride and cuprous iodide are used as catalysts, diisopropylethylamine is used as base, and the reaction proceeds for 2-3 hours at room temperature under nitrogen, and then the reaction is carried out at 50-90 □ until the completion of the reaction is determined by thin layer chromatography;

the condition for step d) is that: tetrahydrofuran is used as solvent, and compound 4 and N-chlorosuccinimide are stirred at room temperature under nitrogen until the completion of the reaction is determined by thin layer chromatography;

the condition for step e) is that: at 70-120 □, saturated solution of ammonia in methanol is used as solvent and the reaction is carried out overnight in a sealed tube; or compound 4 or 6 reacts directly with concentrated ammonia water by stirring overnight in a sealed tube at 70-120□, wherein the structural formula of the substituted aromatic alkyne 8 is as follows:

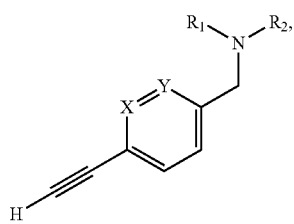

wherein, $R_1$, $R_2$, $R_3$, $R_4$, X and Y are defined as above.

The invention provides different methods for the preparation of the substituted aromatic alkyne 8 and the synthetic route is the following as shown in route 1 or route 2:

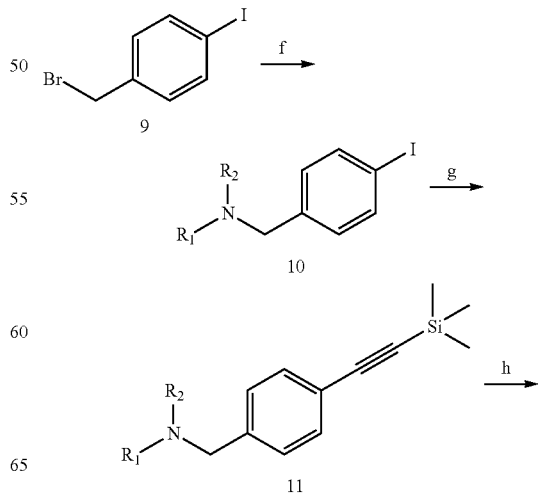

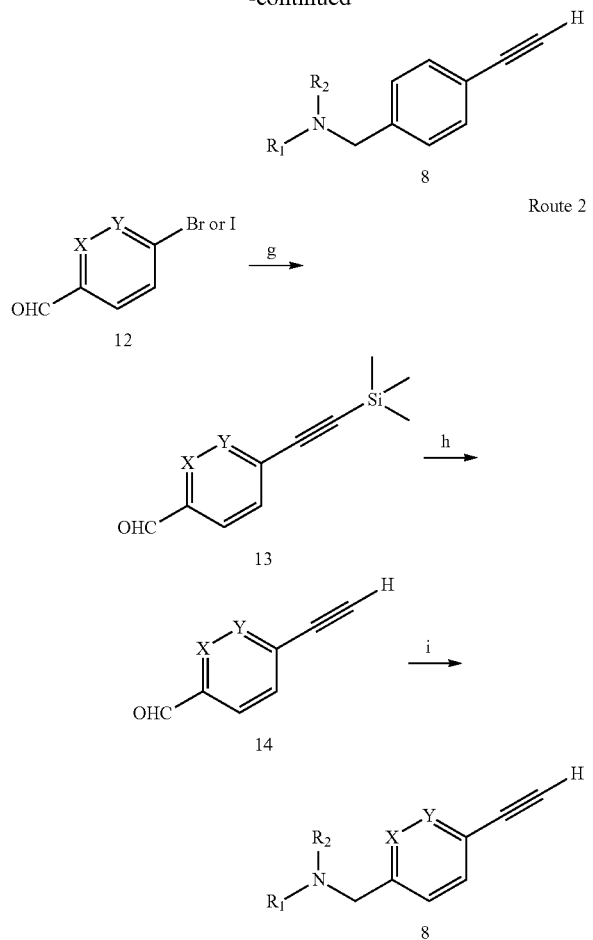

Route 2 f) compound 9 is subjected to an amine substitution reaction to form compound 10;

g) compound 10 or 12 is subjected to a Sonogashira reaction to form compound 11 or 13, respectively;

h) compound 11 or 13 is subjected to deprotection to form compound 8 or 14, respectively;

i) compound 14 is subjected to reductive amination to form compound 8;

the condition of step f) is that: the saturated solution of C1-C4 alkyl amine or five-membered/six-membered secondary amine containing at least one heteroatom (O/N/S) in alcohol is used as solvent and the reaction mixture is stirred at room temperature;

the condition of step g) is that: tetrahydrofuran is used as solvent, bis(triphenylphosphine)palladium(II) dichloride and cuprous iodide are used as catalyst, diisopropylethylamine is used as base, and compound 10 or 12 reacts with ethynyltrimethylsilane at reflux under nitrogen;

the condition of step h) is that: methanol is used as solvent, potassium carbonate is used as base and the reaction mixture is stirred at room temperature;

the condition of step i) is that: methanol is used as solvent, sodium cyanoborohydride is used as reduction agent, and compound 14 reacts with various amines under stirring at room temperature;

wherein, R1, R2, X and Y are defined as above.

Another object of the invention is to provide a use of the compound of general formula I or the pharmacologically or physiologically acceptable salts thereof in the preparation of medicaments for PARP related diseases, such as anti-tumor, anti-inflammatory medicament.

DETAILED DESCRIPTION

The structure and preparation method of the compounds in the present invention and the in vitro and in vivo PARP1/2-inhibiting activity thereof will be further illustrated by combining with the following examples. However, these examples are intended to illustrate the invention, but not limit the invention in any way.

In all examples, 5-fluorosalicylic acid is supplied by Shanghai Bepharm, Ltd.; bis(triphenylphosphine) palladium (II) dichloride is supplied by Shanghai Chiral Chemistry Co., Ltd.; trimethylsilylacetylene is supplied by Dalian Research & Design Institute of Chemical Industry; 4-bromobenzaldehyde is supplied by Shanghai Bangcheng Chemical Co., Ltd.; and N-iodosuccinimide is supplied by Shanghai Darui Chemical Co., Ltd. The initial reagents, solvents and materials are supplied by Sinopharm Chemical Reagent Co., Ltd unless otherwise indicated. The microwave reaction is carried out in CEM NULL microwave reactor; $^1$HNMR is recorded by Brucher AM-400 or GEMINI-300 nuclear magnetic resonance spectrometer wherein chemical shift is represented as δ (ppm); mass spectrometry is recorded by Finnigan MAT-95 mass spectrometer or Agilent 1200-6110 type single quadrupole LC/MS and melting point is measured by Buchi 510 melting point apparatus wherein temperature is not corrected. The silica gel of separation is 200-300 mesh for column chromatography from Qingdao Marine Chemical Plant. In the specification, the chemical reagents represented by English abbreviation are as follows:

NBS N-bromosuccinimide
NIS N-iodosuccinimide
NCS N-chlorosuccinimide
DMF N,N-dimethylformamide
DIPEA diisopropylethylamine
THF tetrahydrofuran Preparation and Synthesis of the Compounds Example 1

Preparation of methyl 5-fluorosalicylate (compound 2a)

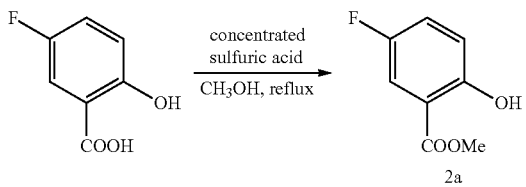 [SMILES: O=C(O)c1cc(F)ccc1O ; COC(=O)c1cc(F)ccc1O]

10 g (0.064 mol) of 5-fluorosalicylic acid was dissolved into 60 mL methanol in a 250 mL round-bottom flask with a magnetic stirrer. 5 mL of concentrated sulfuric acid was added dropwise under the ice bath. Upon addition, the mixture was heated under reflux condensation overnight in an oil bath at 80□. On the next day the reaction mixture was cooled to room temperature and methanol was removed under reduced pressure by rotary evaporator. 60 mL of ethyl acetate was added to the residue and the organic layer was washed with 50 mL of saturated sodium bicarbonate solution and 50 mL of saturated sodium chloride solution in turn. Then the organic layer was dried on anhydrous sodium sulfate and evaporated to dryness. The residue was purified by column chromatography (silica gel, petroleum ether/ethyl acetate=150:1) to afford 10.0 g product as a light color oil in 92% yield. Then the oil solidified to be strip crystal when pumping to dryness by oil pump.

$^1$HNMR (300 MHz, CDCl$_3$) δ 10.51 (s, 1H), 7.50 (dd, J=3.3, 8.7 Hz, 1H), 7.22-7.15 (m, 1H), 6.94 (q, J=4.5Hz, 1H), 3.96 (s, 3H); MS (EI) M$^+$: m/z (%) 170 (50).

Preparation of methyl 5-fluoro-3-iodosalicylate (compound 3a)

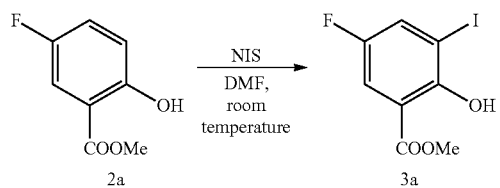 [SMILES: COC(=O)c1cc(F)ccc1O ; "NIS" ; COC(=O)c1cc(F)cc(I)c1O]

7 g (0.041 mol) of methyl 5-fluorosalicylate (compound 2a) was dissolved in 40 mL of DMF in a 100 mL round-bottom flask with a magnetic stirrer. 11.1 g (0.049 mol, 1.2 eq) of NIS was added and the reaction mixture was stirred over weekend under nitrogen at room temperature. After the reaction was finished, 80 mL of ethyl acetate was added to the mixture and the organic layer was washed with 50 mL of saturated sodium chloride solution twice. Then the organic layer was dried on anhydrous sodium sulfate and evaporated to dryness. The residue was purified by column chromatography (silica gel, petroleum ether/ethyl acetate=150:1) to afford 10.8 g product as a white flocculent solid in 89% yield.

$^1$H-NMR (300 MHz, CDCl$_3$) δ 11.37 (s, 1H), 7.70 (dd, J=3.3, 7.8 Hz, 1H), 7.56 (dd, J=3.3, 8.7 Hz, 1H), 3.98 (s, 3H); MS (ESI) (M+H)$^+$: m/z (%) 297.0 (55).

Example 2

Preparation of N,N-dimethyl-1-(4-iodophenyl)methylamine (compound 10a)

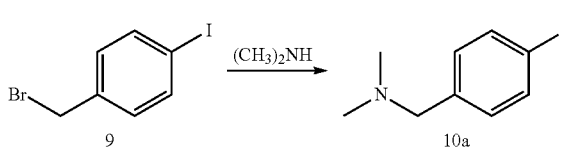

100 mL of dimethylamine aqueous solution was added into a 250 mL round-bottom flask. 12 g (40 mmol) of p-iodobenzyl bromide (compound 9) was added in three batches and stirred overnight at room temperature. The reaction mixture was extracted using ethyl acetate for three times on the next day. The organic layer was dried on anhydrous sodium sulfate and evaporated to dryness by rotary evaporator. 8.4 g of yellow liquid was obtained by column chromatography (silica gel, petroleum ether/ethyl acetate=5 to 1) in 80% yield.

$^1$HNMR (300 MHz, CDCl$_3$) δ 7.63 (d, J=8.1 Hz, 2H), 7.05 (d, J=8.1 Hz, 2H), 3.35 (s, 2H), 2.22 (s, 6H); MS (ESI) (M+H)$^+$: m/z (%) 262.0 (100).

Preparation of N,N-dimethyl-1-{4-[(trimethylsilyl)ethynyl]phenyl}-methanamine (compound 11a)

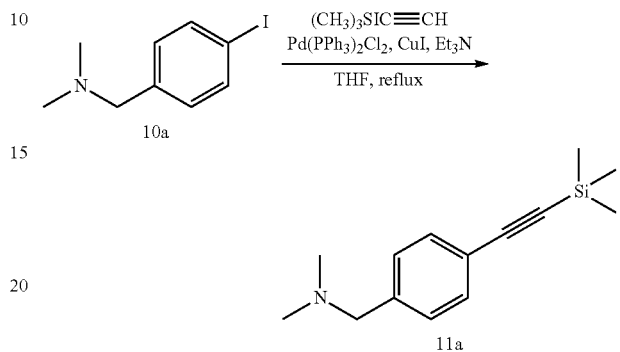

9.03 g (34.5 mmol) of N,N-dimethyl-1-(4-iodophenyl)methylamine (compound 10a), 6.86 g (70 mmol) of trimethylsilylacetylene, 300 mg (0.35 mmol) of bis(triphenylphosphine) palladium(II) dichloride, 133 mg (0.7 mmol) of copper(I) iodide, 10 mL of triethylamine and 100 mL of THF were added into a 250 mL round bottom flask. The flask was vacuumed and filled with nitrogen for three times, and then the reaction was carried out overnight at reflux in an oil bath at 80 □. On the next day, the reaction mixture was cooled to room temperature and most of solvent was removed under reduced pressure by rotary evaporator. The silica gel was added directly to the mixture and then purified by column chromatography (petroleum ether/ethyl acetate=5:1) to provide 6.8 g product as a brown oil in 85% yield.

$^1$HNMR (300 MHz, CDCl$_3$) δ 7.44 (d, J=8.1 Hz, 2H), 7.22 (d, J=8.1 Hz, 2H), 3.39 (s, 2H), 2.21 (s, 6H), 0.24 (s, 9H); MS (ESI) (M+H)$^+$: m/z (%) 232.0 (100).

Preparation of N,N-dimethyl-1-(4-acetylenylphenyl)-methylamine (compound 8a)

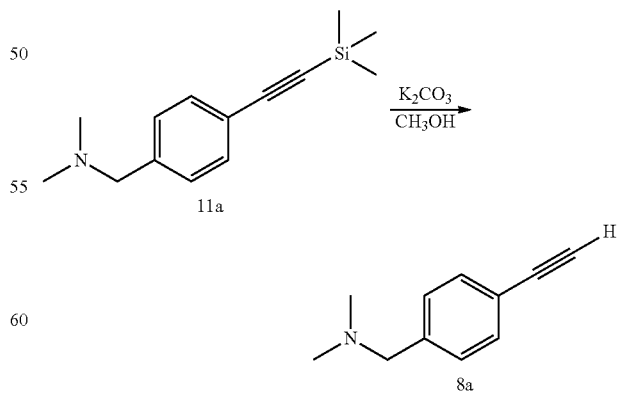

8 g (34.6 mmol) of N,N-dimethyl-1-{4-[(trimethylsilyl)acetylenyl]phenyl}-methylamine (compound 11a) was dissolved into 80 mL of methanol in a 250 mL round bottom flask, and 2.46 g (17.3 mmol) of potassium carbonate was added. The flask was vacuumed and filled with nitrogen for three times, and then the reaction was carried out for two hours at room temperature. After the reaction was finished, most of solvent was removed under reduced pressure by rotary evaporator. 80 mL of ethyl acetate was added and the organic layer was washed with 50 mL of saturated sodium chloride solution. Then the organic layer was dried on anhydrous sodium sulfate and evaporated to dryness. The residue was purified by column chromatography (silica gel, petroleum ether/ethyl acetate=2:1) to afford 4.8 g product as yellow liquid in 87% yield.

$^1$HNMR (300 MHz, CDCl$_3$) δ 7.46 (d, J=8.1 Hz, 2H), 7.25 (d, J=8.1 Hz, 2H), 3.40 (s, 2H), 3.05 (s, 1H), 2.21 (s, 6H); MS (ESI) (M+H)$^+$: m/z (%) 160.2 (100).

Preparation of methyl 5-fluoro-2-{4-[(dimethyl-amino)methyl]phenyl}benzofuran-7-carboxylate (compound 4a)

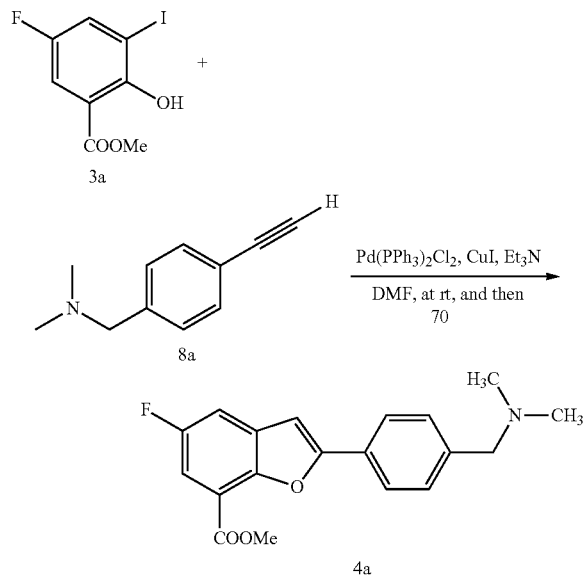

3.4 g (21.4 mmol) of N,N-dimethyl-1-(4-acetylenylphenyl)-methylamine (compound 8a), 3.16 g (10.7 mmol) of methyl 5-fluoro-3-iodosalicylate (compound 3a), 750 mg (1.07 mmol) of bis(triphenylphosphine)palladium(II) dichloride, 203 mg (1.07 mmol) of cuprous iodide, 2.16 g (21.4 mmol) of triethylamine and 10 mL of DMF were added into a 100 mL two-neck round-bottom flask. After the flask was vacuumed and filled with nitrogen for three times, the reaction was carried out for 2 hours at room temperature and then overnight in an oil bath at 70□. On the next day, 60 mL of ethyl acetate was added to the mixture and the organic layer was washed with 50 mL of saturated sodium chloride solution. Then the organic layer was dried on anhydrous sodium sulfate and evaporated to dryness. The residue was purified by column chromatography (silica gel, dichloromethane/methanol=60:1) to afford 1.7 g product as brown oil in 48% yield.

$^1$HNMR (300 MHz, CDCl$_3$) δ 7.90 (d, J=8.7 Hz, 2H), 7.64 (dd, J=3.0, 9.3 Hz, 1H), 7.54 (d, J=8.1 Hz, 2H), 7.43 (dd, J=3.0, 8.1 Hz, 1H), 7.04 (s, 1H), 4.05 (s, 3H), 3.73 (s, 2H), 2.44 (s, 6H); MS (ESI) (M+H)$^+$: m/z (%) 328.2 (100).

Preparation of 5-fluoro-2-{4-[(dimethylamino) methyl]phenyl}benzofuran-7-carboxamide (compound 5a)

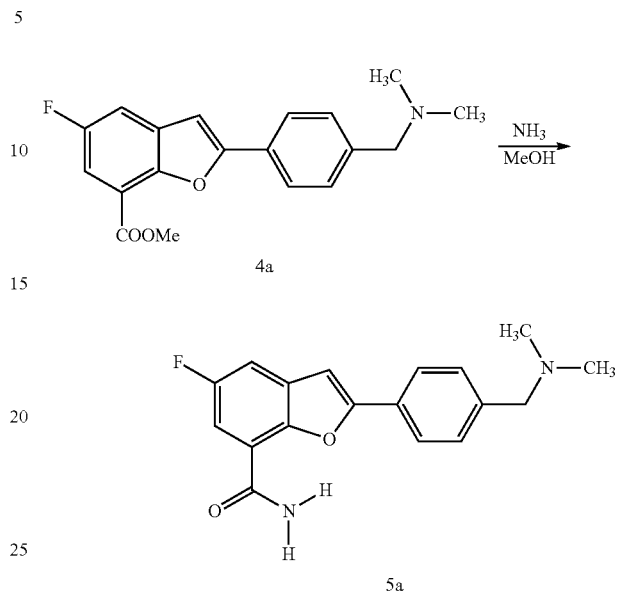

1.65 g (5 mmol) of methyl 5-fluoro-2-{4-[(dimethyl-amino)methyl]phenyl}benzofuran-7-carboxylate (compound 4a) and 50 mL of saturated ammonia solution of methanol were loaded into a 100 mL sealed tube and reacted overnight in an oil bath at son. On the next day, the reaction mixture was cooled to room temperature and settled to precipitate needle-shaped crystals. 1.18 g of light yellow needle-shaped crystals was obtained by filtrating and washing with methanol in 75% yield.

$^1$HNMR (300 MHz, d$_6$-DMSO) δ 7.98-7.60 (m, 3H), 7.89 (br s, 1H), 7.66 (dd, J=3.0, 8.7 Hz, 1H), 7.49-7.43 (m, 4H), 3.45 (s, 2H), 2.17 (s, 6H); MS (ESI) (M+H)$^+$: m/z (%) 313.2 (100).

Example 3

Preparation of N-methyl-1-(4-iodophenyl)methylamine (compound 10b)

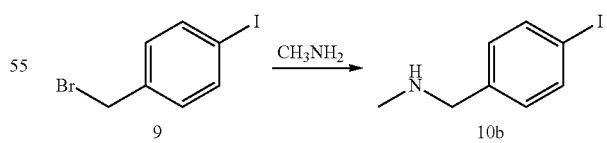

13.8 g of yellow liquid was obtained in 83% yield according to the preparation process of compound 10a, wherein 20 g (67 mmol) of p-iodobenzyl bromide (compound 9) was used as a reactant.

$^1$HNMR (300 MHz, CDCl$_3$) δ 7.63 (d, J=8.1 Hz, 2H), 7.06 (d, J=8.1 Hz, 2H), 3.68 (s, 2H), 2.43 (s, 3H); MS (ESI) (M+H)$^+$: m/z (%) 248 (61).

19

Preparation of N-methyl-1-{4-[(trimethylsilyl)acetylenyl]phenyl}-methylamine (compound 11 b)

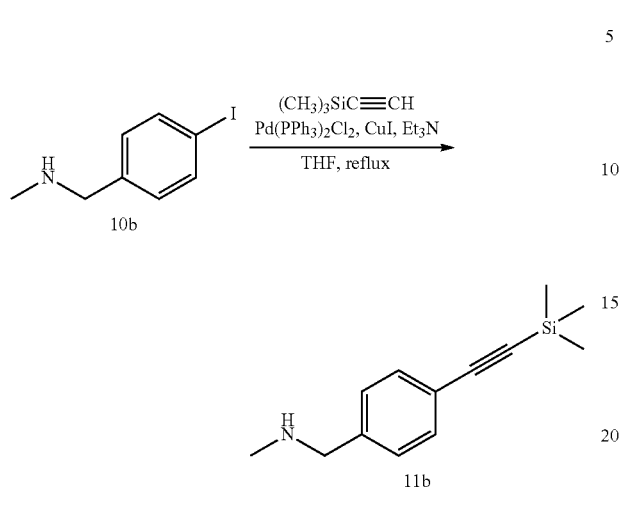

9.1 g of brown solid was obtained in 80% yield according to the preparation process of compound 11a, wherein 13 g (52.6 mmol) of N-methyl-1-(4-iodophenyl)methylamine (compound 10b) was used as a reactant.

MS (ESI) (M+H)$^+$: m/z (%) 218.2 (87).

Preparation of N-methyl-1-(4-acetylenylphenyl)-methylamine (compound 8b)

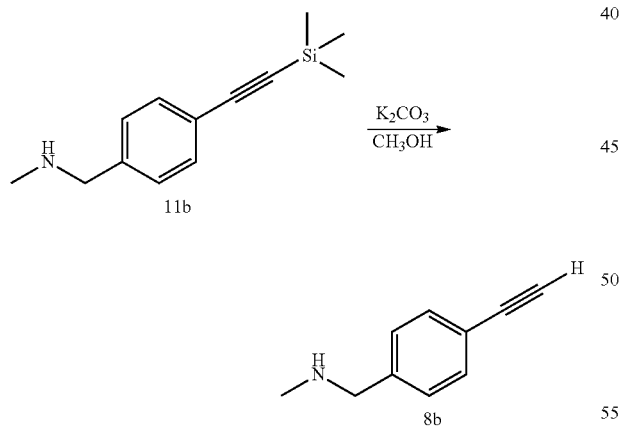

4.6 g of brown liquid was obtained in 86% yield according to the preparation process of compound 8a, wherein 8 g (36.8 mmol) of N-methyl-1-{4-[(trimethylsilyl)acetylenyl]phenyl}-methylamine (compound 11b) was used as a reactant.

$^1$HNMR (300 MHz, d$_6$-DMSO) δ 7.41 (d, J=8.1 Hz, 2H), 7.32 (d, J=8.1Hz, 2H), 4.10 (s, 1H), 3.64 (br s, 2H), 2.24 (br s, 3H); MS (ESI) (M+H)$^+$: m/z (%) 146.1 (10).

20

Preparation of methyl 5-fluoro-2-{4-[(methylamino)methyl]phenyl}benzofuran-7-carboxylate (compound 4b)

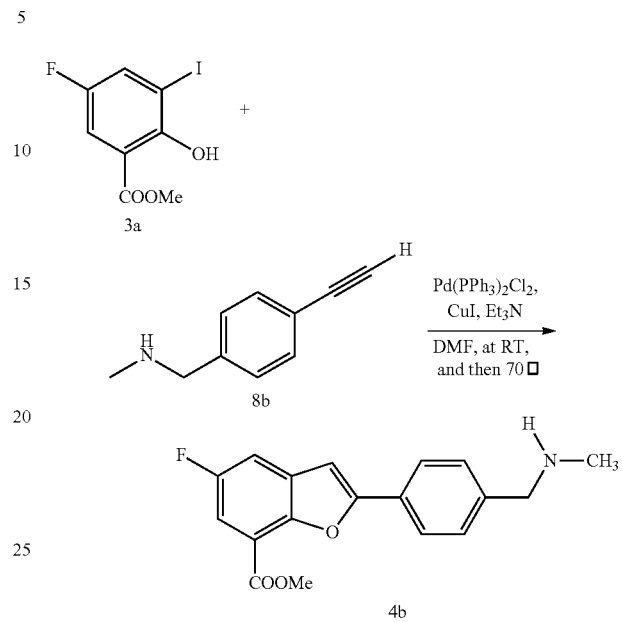

3.2 g of brown oil was obtained in 51% yield according to the preparation process of compound 4a, wherein 3.19 g (22 mmol) of N-methyl-1-(4-acetylenylphenyl)-methylamine (compound 8b) and 5.92 g (20 mmol) of methyl 5-fluoro-3-iodosalicylate (compound 3a) were used as reactants.

$^1$HNMR (300 MHz, CDCl$_3$) δ 7.86 (d, J=8.7 Hz, 2H), 7.62 (dd, J=2.7, 9.6 Hz, 1H), 7.44-7.41 (m, 3H), 7.00 (s, 1H), 4.05 (s, 3H), 3.82 (s, 2H), 3.48 (s, 1H), 2.49 (s, 3H); MS (ESI) (M+H)$^+$: m/z (%) 314.1 (30).

Preparation of 5-fluoro-2-{4-[(methylamino)methyl]phenyl}benzofuran-7-carboxamide (compound 5b)

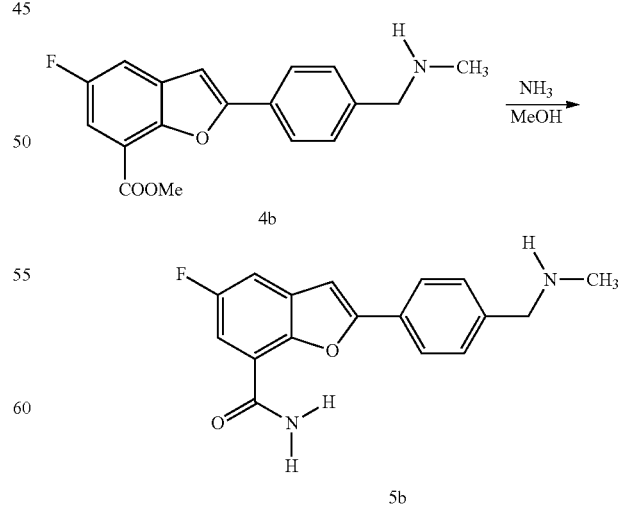

1.81 g of beige granulous solid was obtained in 70% yield according to the preparation process of compound 5a, wherein 2.7 g (8.6 mmol) of methyl 5-fluoro-2-{4-[(methylamino)methyl]phenyl}benzofuran-7-carboxylate (compound 4b) was used as a reactant.

¹HNMR (300 MHz, d₆-DMSO) δ 7.97-7.94 (m, 3H), 7.88 (br s, 1H), 7.64 (dd, J=2.7, 8.4 Hz, 1H), 7.50-7.42 (m, 4H), 3.70 (s, 2H), 2.28 (s, 3H); MS (EI) (M): m/z (%) 298 (100).

Example 4

Preparation of N-methyl-1-(4-acetylenylphenyl)-methylamine (compound 8b)

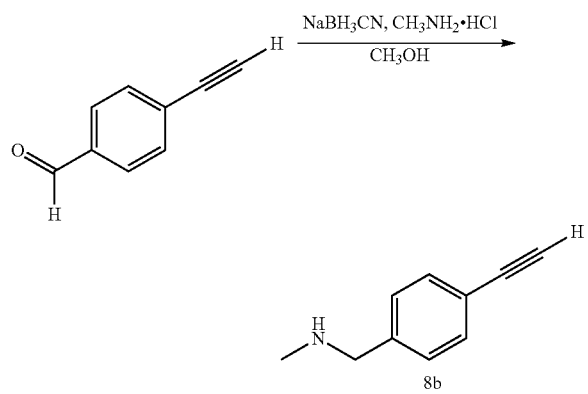

238 mg (1.5 mmol) of 4-acetylenylbenzaldehyde was dissolved into 10 mL of methanol in a 100 mL round bottom flask, then 101 mg (1.5 mmol) of methylamine hydrochloride and 142 mg (2.25 mmol) of sodium cyanoborohydride were added. The reaction was carried out at room temperature for 3 hours. After the reaction was finished, water was added and the pH value was adjusted to 10 by dilute sodium hydroxide solution. Extracted the solution with 50 mL of ethyl acetate and the organic layer was washed with 30 mL of saturated sodium chloride solution. Then the organic layer was dried on anhydrous sodium sulfate and evaporated to dryness. The residue was purified by column chromatography (silica gel, petroleum ether/ethyl acetate=1:1) to afford 133 mg product as brown liquid in 61% yield.

¹HNMR (300 MHz, d₆-DMSO) δ 7.41 (d, J=8.1 Hz, 2H), 7.32 (d, J=8.1Hz, 2H), 4.10 (s, 1H), 3.64 (br s, 2H), 2.24 (br s, 3H); MS (ESI) (M+H)⁺: m/z (%) 146.1 (10).

Example 5

Preparation of methyl 3-chloro-5-fluoro-2-{4-[(dimethylamino)methyl]phenyl}benzofuran-7-carboxylate (compound 6a)

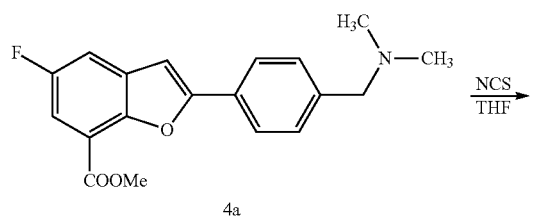

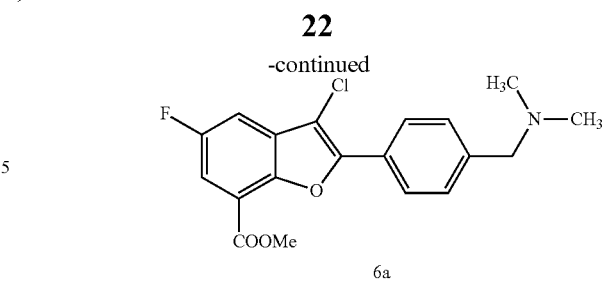

500 mg (1.53 mmol) of methyl 2-{4-[(dimethylamino)methyl]phenyl}-5-fluorobenzofuran-7-carboxylate (compound 4a) was dissolved into 20 mL of tetrahydrofuran in a 100 mL two-neck round bottom flask. 20 mL of NCS (350 mg, 2.6 mmol) solution in tetrahydrofuran was added dropwise into the flask in an ice-bath for 15 minutes. The flask was vacuumed and filled with nitrogen for three times and the reaction was carried out at room temperature overnight. On the next day, 50 mL of ethyl acetate was added to the mixture, and the organic layer was washed with 50 mL of saturated sodium bicarbonate solution and 50 mL of saturated sodium thiosulfate solution respectively. Then the organic layer was dried on anhydrous sodium sulfate and evaporated to dryness. The residue was purified by column chromatography (silica gel, dichloromethane/methanol=80:1) to afford 170 mg product as yellow powder in 31% yield.

¹HNMR (300 MHz, CDCl₃) δ 8.12 (d, J=8.1 Hz, 2H), 7.70 (dd, J=2.7, 9.3 Hz, 1H), 7.47-7.44 (m, 3H), 4.04 (s, 3H), 3.50 (s, 2H), 2.27 (s, 6H); MS (ESI) (M+H)⁺: m/z (%) 362.1 (100), 364.1 (33).

Preparation of 3-chloro-5-fluoro-2-{4-[(dimethylamino)methyl]phenyl}benzofuran-7-carboxamide (compound 7a)

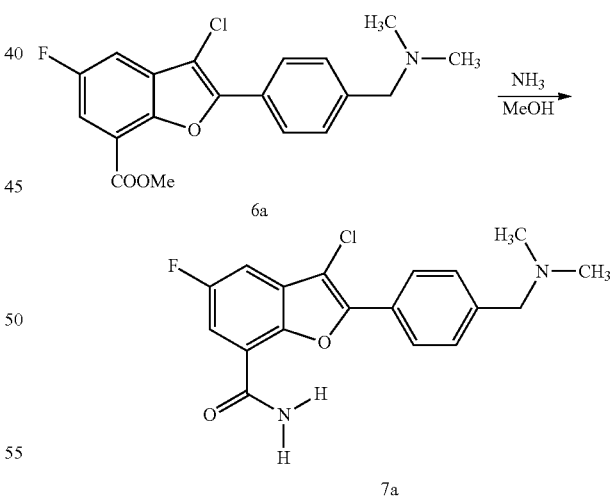

38 mg of off-white powder was obtained in 79% yield according to the preparation process of compound 5a, wherein 50 mg (0.14 mmol) of methyl 3-chloro-5-fluoro-2-{4-[(dimethylamino)methyl]phenyl}benzofuran-7-carboxylate (compound 6a) was used as a reactant.

¹HNMR (300 MHz, CDCl₃) δ 7.99 (d, J=8.7 Hz, 2H), 7.84 (dd, J=2.7, 9.6 Hz, 1H), 7.47 (d, J=8.7 Hz, 2H), 743 (dd, J=2.7, 7.2 Hz, 1H) 6.28 (s, 1H), 3.50 (s, 2H), 2.28 (s, 6H); MS (ESI) (M+H)⁺: m/z (%) 347.1 (100), 349.1 (33).

Example 6

Preparation of 5-[(trimethylsilyl)acetylenyl]pyridyl-2-aldehyde (compound 13a)

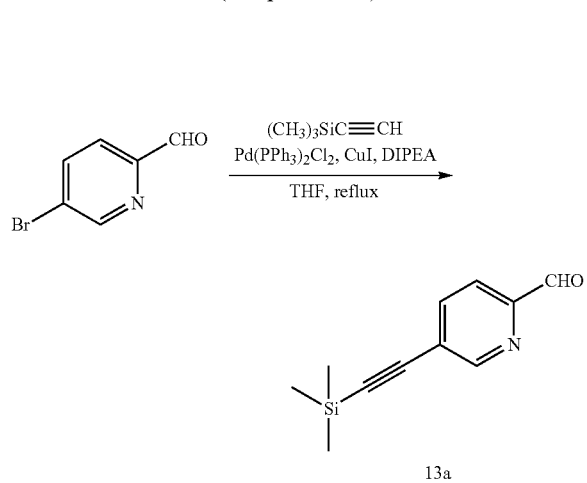

930 mg of brown powder was obtained in 57% yield according to the preparation process of compound 11a, wherein 1.5 g (8 mmol) of 5-bromo-pyridyl-2-aldehyde was used as a reactant.

$^1$HNMR (300 MHz, CDCl$_3$) δ 10.05 (s, 1H), 8.80 (s, 1H), 7.89 (s, 2H), 0.28 (s, 9H); MS (ESI) (M+H)$^+$: m/z (%) 204.1 (64).

Preparation of 5-acetylenyl-pyridyl-2-aldehyde (compound 14a)

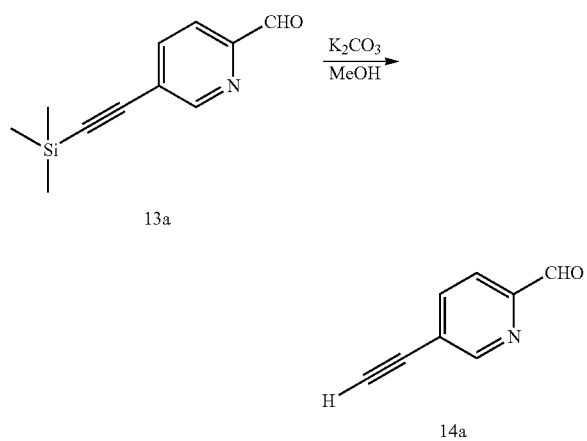

377 mg of light yellow powder was obtained in 72% yield according to the preparation process of compound 8a, wherein 812 mg (4 mmol) of 5-[(trimethylsilyl)acetylenyl]pyridyl-2-aldehyde (compound 13a) was used as a reactant.

$^1$HNMR (300 MHz, CDCl$_3$) δ 10.07 (s, 1H), 8.84 (s, 1H), 7.93 (s, 2H), 3.42 (s, 1H); MS (ESI) (M+H)$^+$: m/z (%) 132.1 (64).

Preparation of N-methyl-1-(5-acetylenyl-2-pyridyl)methylamine (compound 8c)

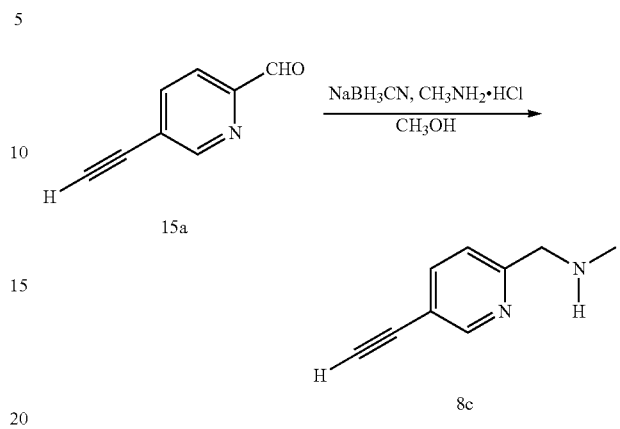

135 mg of brown liquid was obtained in 62% yield according to the preparation process in example 4, wherein 196 mg (1.5 mmol) of 5-acetylenyl-pyridyl-2-aldehyde (compound 14a) was used as a reactant.

$^1$HNMR (300 MHz, CDCl$_3$) δ 8.65 (d, J=1.5 Hz, 1H), 7.73 (dd, J=2.1, 8.1 Hz, 1H), 7.27 (d, J=8.1 Hz, 1H), 3.87 (s, 2H), 3.18 (s, 1H), 2.46 (s, 3H); MS (ESI) (M+H)$^+$: m/z (%) 147.1 (100).

Preparation of methyl 5-fluoro-2-{6-[(methylamino)methyl]-3-pyridyl}benzofuran-7-carboxylate (compound 4c)

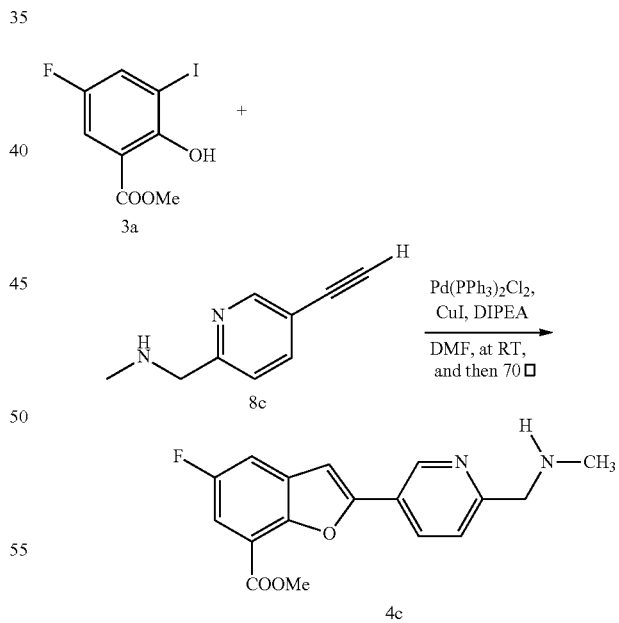

10 mg of light yellow powder was obtained in 5.7% yield according to the preparation process of compound 4a, wherein 82 mg (0.56 mmol) of N-methyl-1-(5-acetylenyl-2-pyridyl)methylamine (compound 8c) and 166 mg (0.56 mmol) of methyl 5-fluoro-3-iodosalicylate (compound 3a) were used as reactants.

$^1$HNMR (300 MHz, CDCl$_3$) δ 9.07 (d, J=1.8 Hz, 1H), 8.15 (dd, J=2.1, 8.4 Hz, 1H), 7.66 (dd, J=2.1, 8.4 Hz, 1H), 7.47-7.42 (m, 2H), 7.10 (s, 1H), 4.05 (s, 3H), 3.94 (s, 2H), 2.51 (s, 3H); MS (ESI) (M+H)+: m/z (%) 315.1 (100).

Preparation of 5-fluoro-2-{6-[(methylamino)methyl]-3-pyridyl}benzofuran-7-carboxamide (compound 5c)

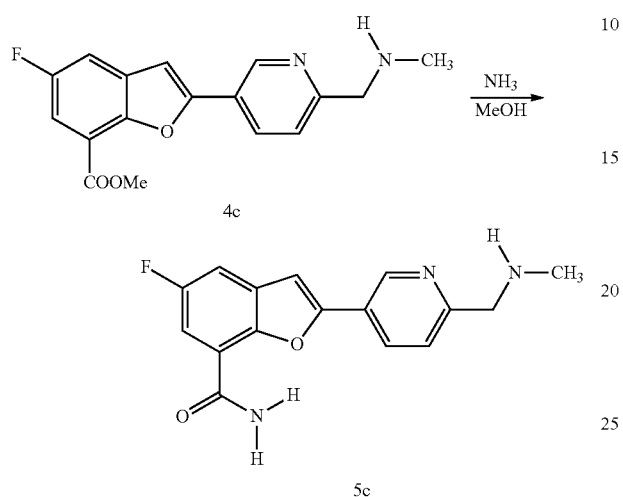

5 mg of white powder was obtained in 52.5% yield according to the preparation process of compound 5a, wherein 10 mg (0.032 mmol) of methyl 5-fluoro-2-{6-[(methylamino)methyl]-3-pyridyl}benzofuran-7-carboxylate (compound 4c) was used as a reactant.

¹HNMR (300 MHz, CD₃OD) δ 9.09 (s, 1H), 8.32 (dd, J=2.1, 8.1 Hz, 1H), 7.58-7.51 (m, 3H), 7.44 (s, 1H), 3.96 (s, 2H), 2.49 (s, 3H); MS (ESI) (M+H)+: m/z (%) 300.1 (100).

Example 7

Preparation of 6-[(trimethylsilyl)acetylenyl]pyridyl-3-aldehyde (compound 13b)

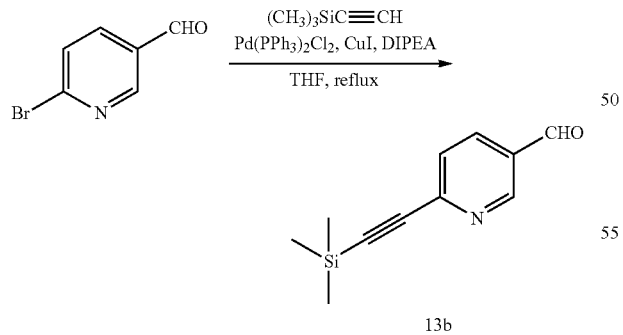

222 mg of yellow powder was obtained in 73% yield according to the preparation process of compound 11a, wherein 279 mg (1.5 mmol) of 6-bromo-pyridyl-3-aldehyde was used as a reactant.

¹HNMR (300 MHz, CDCl₃) δ 10.09 (s, 1H), 9.01 (s, 1H), 8.12 (dd, J=1.2, 8.1 Hz, 1H), 7.59 (d, J=1.2 Hz, 1H), 0.28 (s, 9H); MS (ESI) (M+H)+: m/z (%) 204.1 (22).

Preparation of 6-acetylenyl-pyridyl-3-aldehyde (compound 14b)

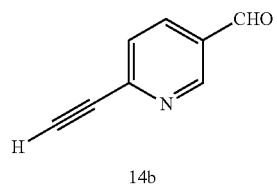

175 mg of white flocculent solid was obtained in 89% yield according to the preparation process of compound 8a, wherein 304 mg (1.5 mmol) of 6-[(trimethylsilyl)acetylenyl]pyridyl-3-aldehyde (compound 13b) was used as a reactant.

¹HNMR (300 MHz, CDCl₃) δ 10.12 (s, 1H), 9.04 (d, J=0.9 Hz, 1H), 8.15 (dd, J=2.1, 8.1 Hz, 1H), 7.63 (d, J=8.1 Hz, 1H), 3.39 (s, 1H); MS (ESI) (M+H)+: m/z (%) 132.1 (59).

Preparation of N-methyl-1-(6-acetylenyl-3-pyridyl)methylamine (compound 8d)

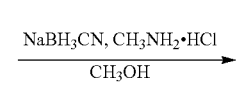

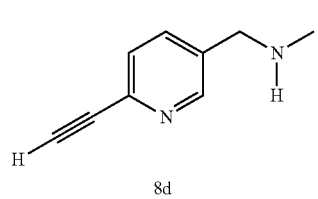

76 mg of brown oil was obtained in 35% yield according to the preparation process in example 4, wherein 196 mg (1.5 mmol) of 6-acetylenyl-pyridyl-3-aldehyde (compound 14b) was used as a reactant.

¹HNMR (300 MHz, CDCl₃) δ 8.52 (d, J=2.1 Hz, 1H), 7.65 (dd, J=2.1, 8.4 Hz, 1H), 7.45 (d, J=8.4 Hz, 1H), 3.77 (s, 2H), 3.12 (s, 1H), 2.45 (s, 3H); MS (ESI) (M+H)+: m/z (%) 147.1 (100).

Preparation of methyl 5-fluoro-2-{5-[(methylamino)methyl]-2-pyridyl}benzofuran-7-carboxylate (compound 4d)

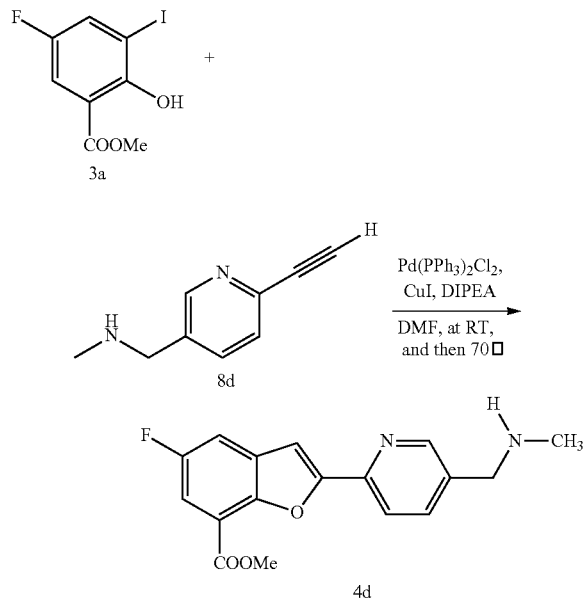

71 mg of brown powder was obtained in 45% yield according to the preparation process of compound 4a, wherein 73 mg (0.50 mmol) of N-methyl-1-(6-acetylenyl-3-pyridyl)methylamine (compound 8d) and 148 mg (0.50 mmol) of methyl 5-fluoro-3-iodosalicylate (compound 3a) were used as reactants.

$^1$HNMR (300 MHz, CDCl$_3$) δ 8.62 (s, 1H), 7.99 (d, J=7.1 Hz, 1H), 7.81 (dd, J=1.8, 7.1 Hz, 1H), 7.67 (dd, J=2.7, 9.6 Hz, 1H), 7.49 (dd, J=2.4, 8.7 Hz, 1H), 7.44 (s, 1H), 4.05 (s, 3H), 3.84 (s, 2H), 2.49 (s, 3H); MS (ESI) (M+H)$^+$: m/z (%) 315.1 (100).

Preparation of 5-fluoro-2-{5-[(methylamino)methyl]-2-pyridyl}benzofuran-7-carboxamide (compound 5d)

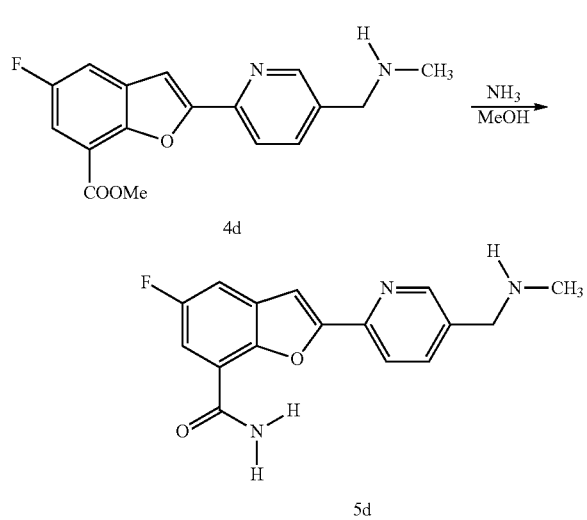

37 mg of light brown powder was obtained in 78% yield according to the preparation process of compound 5a, wherein 50 mg (0.16 mmol) of methyl 2-{5-[(methylamino)methyl]-2-pyridyl}-5-fluorobenzofuran-7-carboxylate (compound 4d) was used as a reactant.

$^1$HNMR (300 MHz, CD$_3$OD) δ 8.63 (s, 1H), 8.06 (d, J=8.4 Hz, 1H), 7.94 (dd, J=1.8, 8.1 Hz, 1H), 7.67-7.58 (m, 3H), 3.82 (s, 2H), 2.43 (s, 3H); MS (ESI) (M+H)$^+$: m/z (%) 300.1 (100).

Example 8

Preparation of 2-fluoro-4-[(trimethylsilyl)acetylenyl]benzaldehyde (compound 13c)

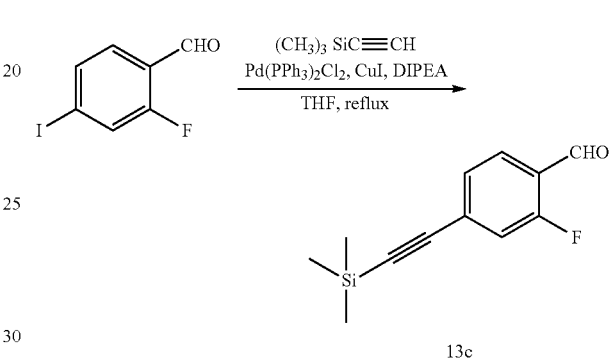

495 mg of brown oil was obtained in 56% yield according to the preparation process of compound 11a, wherein 1 g (4 mmol) of 3-fluoro-4-iodobenzaldehyde was used as a reactant.

$^1$HNMR (300 MHz, CDCl$_3$) δ 10.32 (s, 1H), 7.79 (t, J=7.8 Hz, 1H), 7.32 (d, J=7.8 Hz, 1H), 7.24 (m, 1H), 0.26 (s, 9H); MS (ESI) (M+H)$^+$: m/z (%) 221.0 (10).

Preparation of 4-acetylenyl-2-fluorobenzaldehyde (compound 14c)

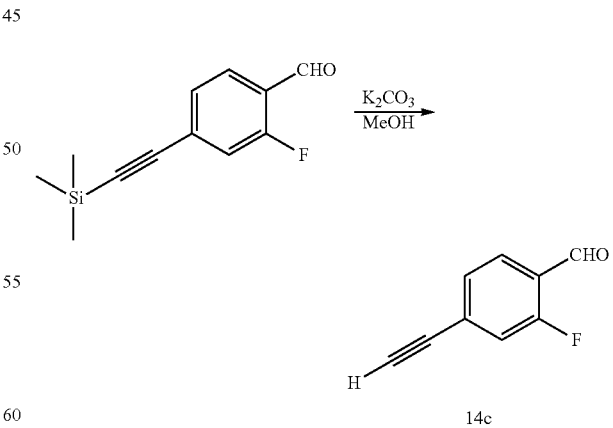

208 mg of yellow solid was obtained in 70% yield according to the preparation process of compound 8a, wherein 440 mg (2 mmol) of 2-fluoro-4-[(trimethylsilyl)acetylenyl]benzaldehyde (compound 13c) was used as a reactant.

$^1$HNMR (300 MHz, CDCl$_3$) δ 10.34 (s, 1H), 7.83 (t, J=7.8 Hz, 1H), 7.37 (d, J=7.8 Hz, 1H), 7.28 (d, J=7.8 Hz, 1H), 3.34 (s, 1H).

Preparation of N-methyl-1-(4-acetylenyl-2-fluorophenyl)methylamine (compound 8e)

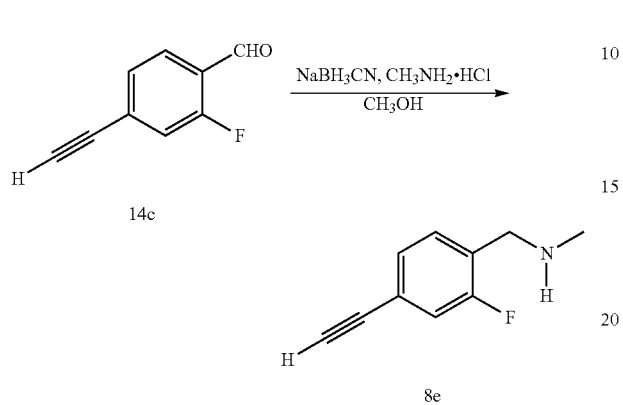

95 mg of yellow oil was obtained in 42% yield according to the preparation process in example 4, wherein 208 mg (1.4 mmol) of 4-acetylenyl-2-fluorobenzaldehyde (compound 14c) was used as a reactant.
MS (ESI) (M+H)$^+$: m/z (%) 164.1 (38).

Preparation of methyl 5-fluoro-2-{4-[(methylamino)methyl]-3-fluorophenyl}benzofuran-7-carboxylate (compound 4e)

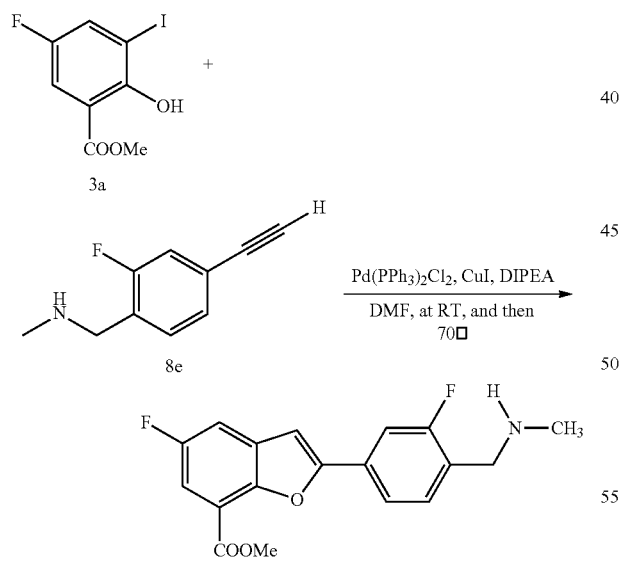

58 mg of yellow viscous liquid was obtained in 34% yield according to the preparation process of compound 4a, wherein 95 mg (0.58 mmol) of N-methyl-1-(4-acetylenyl-2-fluorophenyl)methylamine (compound 8e) and 156 mg (0.52 mmol) of methyl 5-fluoro-3-iodosalicylate (compound 3a) were used as reactants.
MS (ESI) (M+H)$^+$: m/z (%) 332.1 (100).

Preparation of 5-fluoro-2-{4-[(methylamino)methyl]-3-fluorophenyl}benzofuran-7-carboxamide (compound 5e)

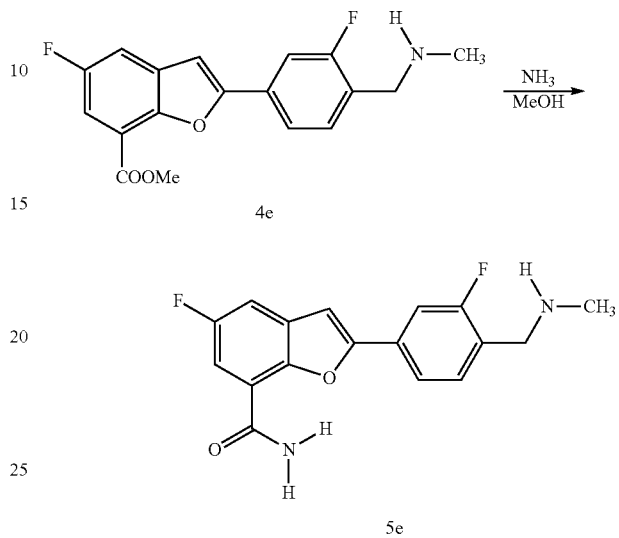

24 mg of light yellow powder was obtained in 43% yield according to the preparation process of compound 5a, wherein 58 mg (0.17 mmol) of methyl 5-fluoro-2-{4-[(methylamino)methyl]-3-fluorophenyl}benzofuran-7-carboxylate (compound 4e) was used as a reactant.
$^1$HNMR (300 MHz, CD$_3$OD) δ 7.83-7.76 (m, 2H), 7.64 (t, J=7.8 Hz, 1H), 7.57-7.50 (m, 2H), 7.41 (s, 1H), 4.22 (s, 2H), 2.71 (s, 3H); MS (ESI) (M+H)$^+$: m/z (%) 317.2 (100).

Example 9

Preparation of 1-(4-ethynylbenzyl)pyrrolidine (compound 8f)

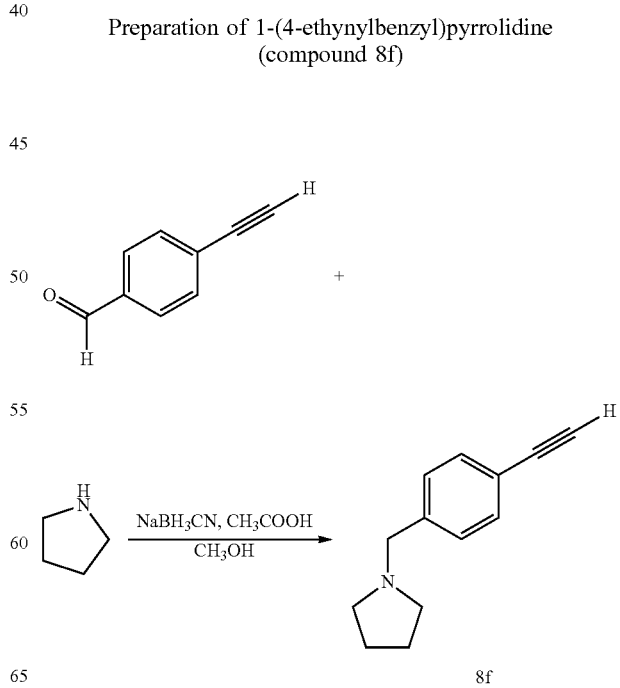

130 mg (1 mmol) of 4-ethynylbenzaldehyde was dissolved into 10 mL methanol in a 50 mL round bottom flask. Then 71 mg (1 mmol) of pyrrolidine, 126 mg (2 mmol) of sodium cyanoborohydride and 120 mg (2 mmol) of glacial acetic acid were added and the reaction was carried out for three hours at room temperature. After the reaction was finished, water was added and the pH value was adjusted to 10 by dilute sodium hydroxide solution. 50 mL of ethyl acetate was added for extraction and the organic layer was washed with 30 mL of saturated sodium chloride solution, dried on anhydrous sodium sulfate and evaporated to dryness by rotary evaporator in sequence. The residue was purified by column chromatography (silica gel, dichloromethane/methanol=30:1) to provide 130 mg product as colourless liquid in 70% yield. $^1$HNMR (300 MHz, CDCl$_3$) δ 7.44 (d, J=7.5 Hz, 2H), 7.28 (d, J=8.4 Hz, 2H), 3.62 (s, 2H), 3.04 (s, 1H), 2.51 (m, 4H), 1.79 (m, 4H); MS (ESI) (M+H)$^+$: m/z (%) 186.2 (100).

Preparation of methyl 5-fluoro-2-{4-[(pyrrolidin-1-yl)methyl]phenyl}benzofuran-7-carboxylate (compound 4f)

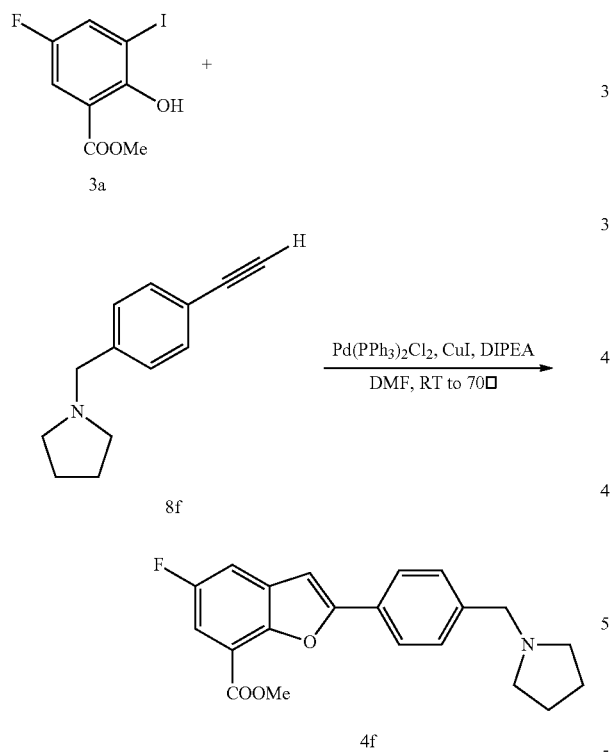

14 mg of brown oil was obtained in 7% yield according to the preparation process of compound 4a, wherein 105 mg (0.57 mmol) of 1-(4-ethynylbenzyl)pyrrolidine (compound 8f) and 168 mg (0.57 mmol) of methyl 5-fluoro-3-iodosalicylate (compound 3a) were used as reactants.

$^1$HNMR (300 MHz, CDCl$_3$) δ 7.85 (d, J=6.3 Hz, 2H), 7.62 (dd, J=2.1, 7.1Hz, 1H), 7.45-7.41 (m, 3H), 7.00 (s, 1H), 4.05 (s, 3H), 3.67 (s, 2H), 2.54 (m, 4H), 1.80 (m, 4H); MS (ESI) (M+H)$^+$: m/z (%) 354.2 (100).

Preparation of 5-fluoro-2-{4-[(pyrrolidin-1-yl)methyl]phenyl}benzofuran-7-carboxamide (compound 8f)

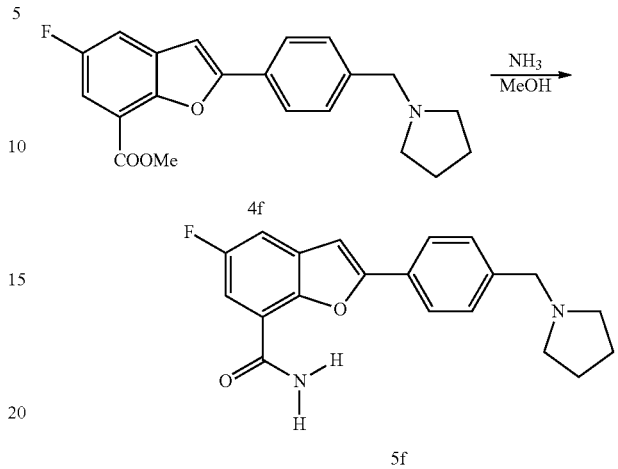

6 mg of white powder was obtained in 52% yield according to the preparation process of compound 5a, wherein 12 mg (0.03 mmol) of methyl 5-fluoro-2-{4-[(pyrrolidin-1-yl)methyl]phenyl}benzofuran-7-carboxylate (compound 4f) was used as a reactant.

$^1$HNMR (300 MHz, CD$_3$OD) δ 7.92 (d, J=8.4 Hz, 2H), 7.47-7.56 (m, 4H), 7.30 (s, 1H), 3.73 (s, 2H), 2.62 (m, 4H), 1.86-1.82 (m, 4H); MS (ESI) (M+H)$^+$: m/z (%) 339.2 (100).

Example 10

Preparation of 1-(4-ethynylbenzyl)-4-methylpiperazine (compound 8g)

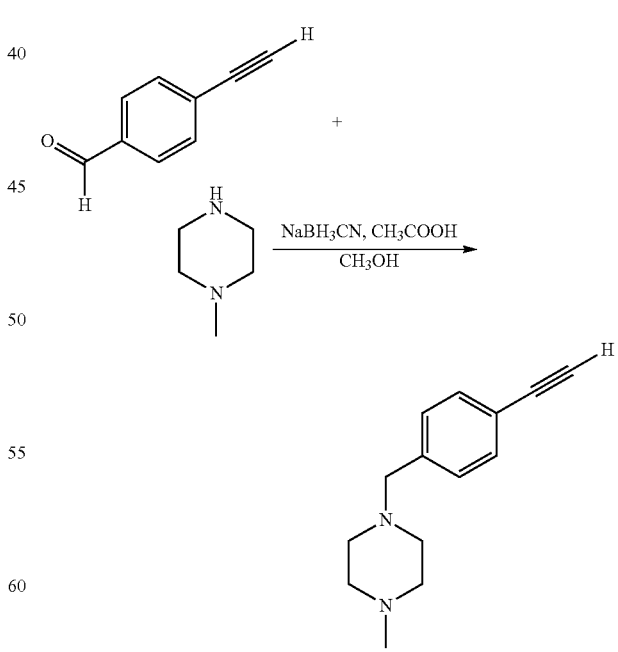

175 mg of yellow liquid was obtained in 68% yield according to the preparation process of compound 8f, wherein 156 mg (1.2 mmol) of 4-ethynylbenzaldehyde and 120 mg (1.2 mmol) of N-methylpiperazine were used as reactants.

¹HNMR (300 MHz, CDCl₃) δ 7.42 (d, J=8.1 Hz, 2H), 7.26 (d, J=8.1 Hz, 2H), 3.49 (s, 2H), 3.05 (s, 1H), 2.44 (br s, 8H), 2.28 (s, 3H); MS (ESI) (M+H)⁺: m/z (%) 215.2 (100).

Preparation of methyl 5-fluoro-2-{4-[(4-methyl-1-piperazino)methyl]phenyl}benzofuran-7-carboxylate (compound 4g)

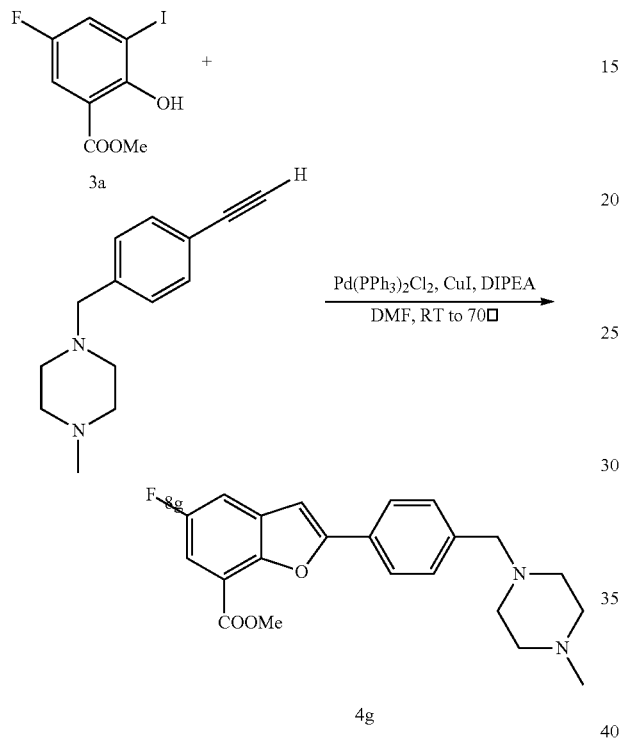

14 mg of brown oil was obtained in 9.4% yield according to the preparation process of compound 4a, wherein 83 mg (0.39 mmol) of 1-(4-ethynylbenzyl)-4-methylpiperazine (compound 8g) and 115 mg (0.39 mmol) of methyl 5-fluoro-3-iodosalicylate (compound 3a) were used as reactants.

¹HNMR (300 MHz, CDCl₃) δ 7.84 (d, J=8.4 Hz, 2H), 7.62 (dd, J=2.4, 9.6 Hz, 1H), 7.44-7.40 (m, 3H), 7.00 (s, 1H), 4.05 (s, 3H), 3.56 (s, 2H), 2.50 (br s, 8H), 2.30 (s, 3H); MS (ESI) (M+H)⁺: m/z (%) 383.2 (100).

Preparation of 5-fluoro-2-{4-[(4-methyl-1-piperazino)methyl]phenyl}benzofuran-7-carboxamide (compound 5g)

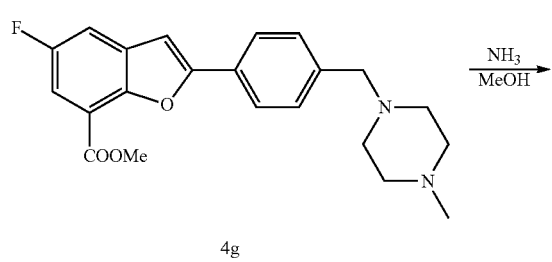

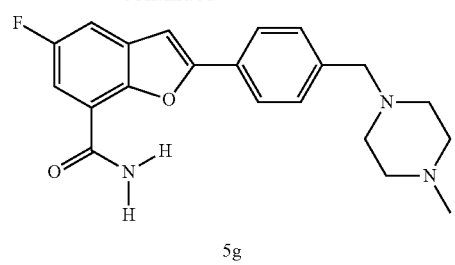

7 mg of white powder was obtained in 73% yield according to the preparation process of compound 18, wherein 10 mg (0.03 mmol) of methyl 5-fluoro-2-{4-[(4-methyl-1-piperazino)methyl]phenyl}benzofuran-7-carboxylate (compound 4g) was used as a reactant.

¹HNMR (300 MHz, CD₃OD) δ 7.90 (d, J=8.1 Hz, 2H), 7.56-7.45 (m, 4H), 7.29 (s, 1H), 3.58 (s, 2H), 2.52 (br s, 8H), 2.28 (s, 3H); MS (ESI) (M+H)⁺: m/z (%) 368.2 (100).

Example 11

Preparation of 1-(4-ethynylbenzyl)piperidine (compound 8h)

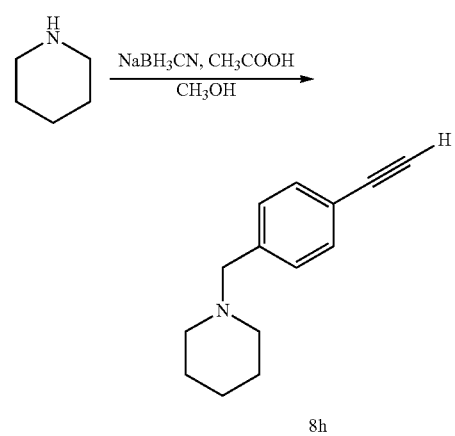

138 mg of yellow liquid was obtained in 58% yield according to the preparation process of compound 8f, wherein 156 mg (1.2 mmol) of 4-ethynylbenzaldehyde and 102 mg (1.2 mmol) of piperidine were used as reactants.

¹HNMR (300 MHz, CDCl₃) δ 7.42 (d, J=8.4 Hz, 2H), 7.27 (d, J=8.1 Hz, 2H), 3.46 (s, 2H), 3.04 (s, 1H), 2.36 (m, 4H), 1.60-1.53 (m, 4H), 1.46-1.40 (m, 2H); MS (ESI) (M+H)⁺: m/z (%) 200.2 (100).

Preparation of methyl 5-fluoro-2-{4-[(piperidin-1-yl)methyl]phenyl}benzofuran-7-carboxylate (compound 4h)

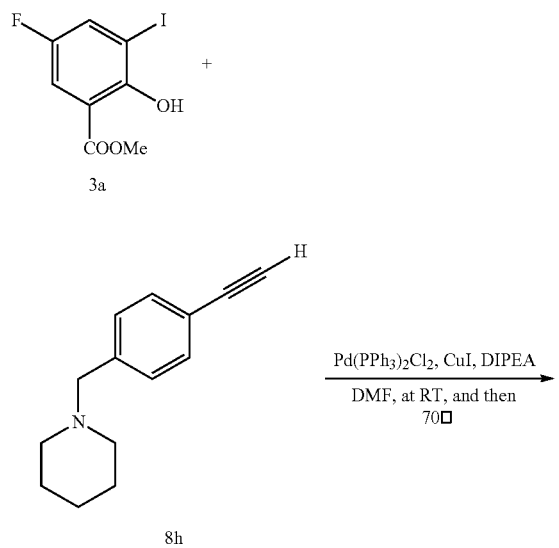

14 mg of colourless oil was obtained in 6.7% yield according to the preparation process of compound 4a, wherein 113 mg (0.57 mmol) of 1-(4-ethynylbenzyl)piperidine (compound 8h) and 140 mg (0.47 mmol) of methyl 5-fluoro-3-iodosalicylate (compound 3a) were used as reactants.

$^1$HNMR (300 MHz, CDCl$_3$) δ 7.85 (d, J=8.1 Hz, 2H), 7.62 (dd, J=2.7, 9.0 Hz, 1H), 7.45-7.41 (m, 3H), 7.00 (s, 1H), 4.05 (s, 3H), 3.53 (s, 2H), 2.41 (m, 4H), 1.63-1.57 (m, 4H), 1.47-1.43 (m, 2H); MS (ESI) (M+H)$^+$: m/z (%) 368.2 (100).

Preparation of 5-fluoro-2-{4-[(piperidin-1-yl)methyl]phenyl}benzofuran-7-carboxamide (compound 5h)

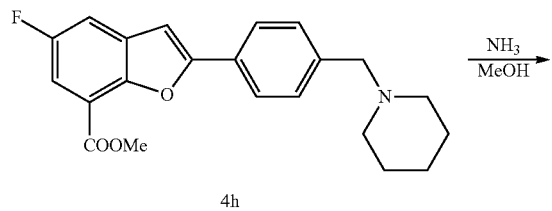

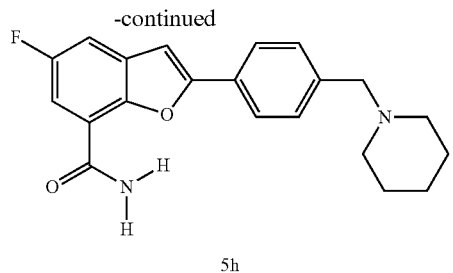

6 mg of white powder was obtained in 52% yield according to the preparation process of compound 5a, wherein 12 mg (0.03 mmol) of methyl 5-fluoro-2-{4-[(piperidin-1-yl)methyl]phenyl}benzofuran-7-carboxylate (compound 4h) was used as a reactant.

$^1$HNMR (300 MHz, CD$_3$OD) δ 7.75-7.66 (m, 3H), 7.44-7.35 (m, 3H), 7.03 (s, 1H), 3.52 (s, 2H), 2.41 (m, 4H), 1.63-1.57 (m, 4H), 1.47-1.43 (m, 2H); MS (ESI) (M+H)$^+$: m/z (%) 353.2 (100).

Example 12

Preparation of 1-(4-ethynylbenzyl)-4-methyl homopiperazine (compound 8i)

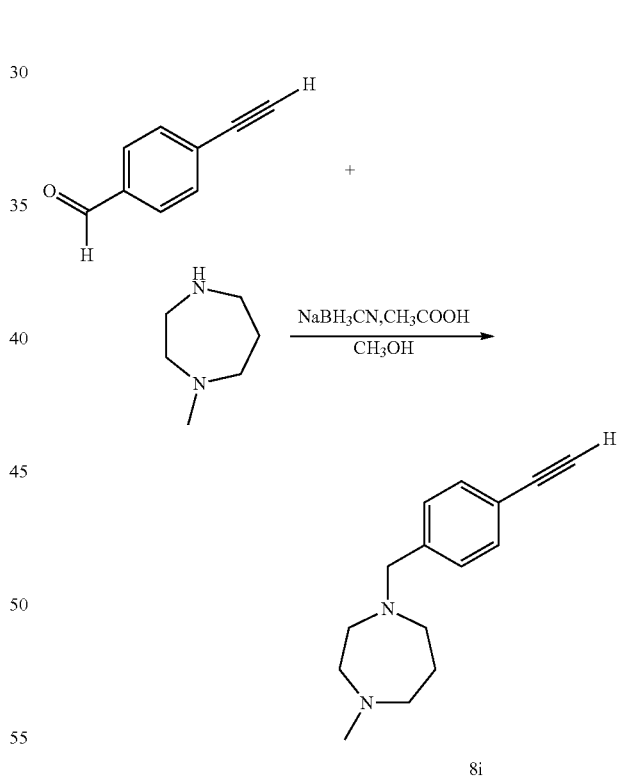

235 mg of yellow liquid was obtained in 86% yield according to the preparation process of compound 8f, wherein 156 mg (1.2 mmol) of 4-ethynylbenzaldehyde and 137 mg (1.2 mmol) of N-methylhomopiperazine were used as reactants.

$^1$HNMR (300 MHz, CDCl$_3$) δ 7.42 (d, J=8.1 Hz, 2H), 7.30 (d, J=8.1 Hz, 2H), 3.62 (s, 2H), 3.04 (s, 1H), 2.71-2.57 (m, 8H), 2.35 (s, 3H), 1.84-1.78 (m, 2H); MS (ESI) (M+H)$^+$: m/z (%) 229.2 (100).

Preparation of methyl 5-fluoro-2-{4-[(4-methyl-1-homopiperazino)methyl]phenyl}-benzofuran-7-carboxylate (compound 4i)

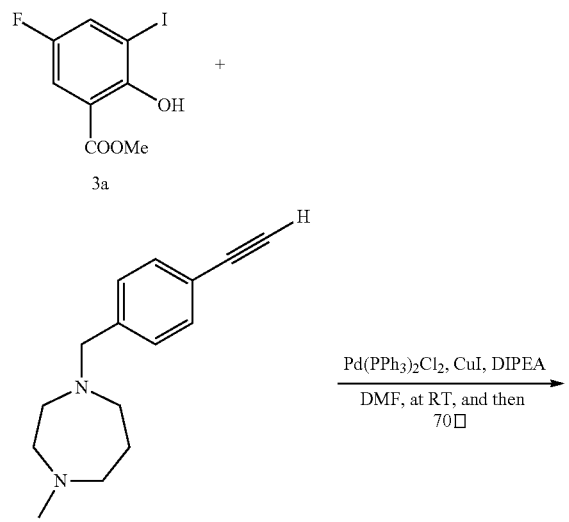

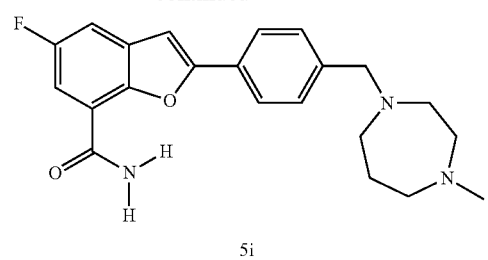

22 mg of brown oil was obtained in 6.4% yield according to the preparation process of compound 4a, wherein 198 mg (0.87 mmol) of 1-(4-ethynylbenzyl)-4-methyl homopiperazine (compound 8i) and 257 mg (0.87 mmol) of methyl 5-fluoro-3-iodosalicylate (compound 3a) were used as reactants.

$^1$HNMR (300 MHz, CDCl$_3$) δ 7.84 (d, J=8.1 Hz, 2H), 7.62 (dd, J=2.4, 9.3 Hz, 1H), 7.54-7.40 (m, 3H), 6.99 (s, 1H), 4.04 (s, 3H), 3.68 (s, 2H), 2.71-2.57 (m, 8H), 2.41 (s, 3H), 1.84-1.78 (m, 2H); MS (ESI) (M+H)$^+$: m/z (%) 397.2 (100).

Preparation of 5-fluoro-2-{4-[(4-methyl-1-homopiperazino)methyl]phenyl}benzofuran-7-carboxamide (compound 5i)

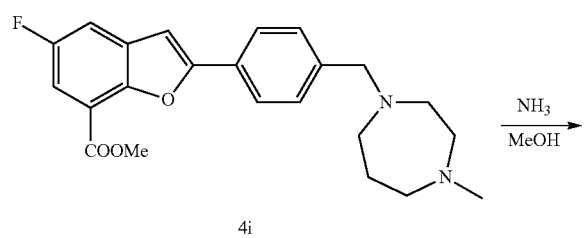

11 mg of white powder was obtained in 76% yield according to the preparation process of compound 5a, wherein 15 mg (0.04 mmol) of methyl 5-fluoro-2-{4-[(4-methyl-1-homopiperazino)methyl]phenyl}-benzofuran-7-carboxylate (compound 4i) was used as a reactant.

$^1$HNMR (300 MHz, CDCl$_3$) δ 7.78-7.72 (m, 3H), 7.47-7.36 (m, 4H), 7.02 (s, 1H), 6.66 (br s, 1H), 3.68 (s, 2H), 2.76-2.64 (m, 8H), 2.38 (s, 3H), 1.88-1.80 (m, 2H); MS (ESI) (M+H)$^+$: m/z (%) 382.2 (100).

Example 13

Preparation of 4-(4-ethynylbenzyl)morpholine (compound 8j)

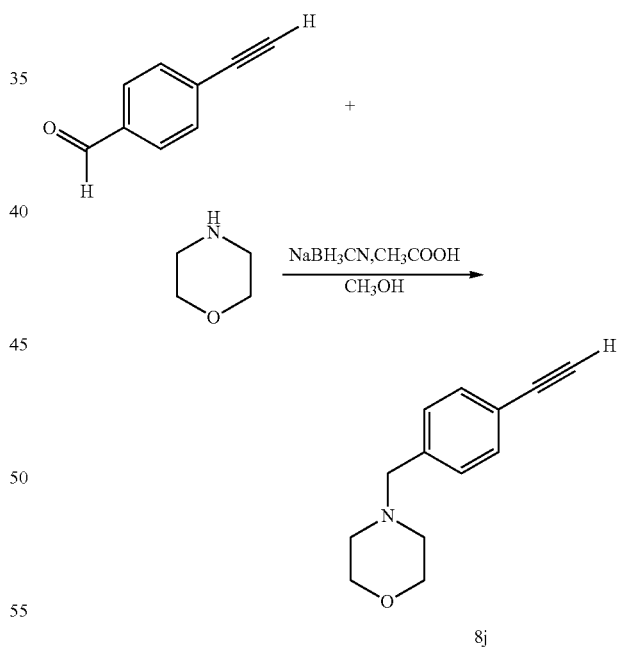

138 mg of yellow liquid was obtained in 57% yield according to the preparation process of compound 8f, wherein 156 mg (1.2 mmol) of 4-ethynylbenzaldehyde and 104 mg (1.2 mmol) of morpholine were used as reactants.

$^1$HNMR (300 MHz, CDCl$_3$) δ 7.43 (d, J=8.4 Hz, 2H), 7.28 (d, J=8.4 Hz, 2H), 3.70 (t, J=5.1 Hz, 4H), 3.48 (s, 2H), 3.05 (s, 1H), 2.43 (t, J=4.8 Hz, 4H); MS (ESI) (M+H)$^+$: m/z (%) 202.1 (100).

Preparation of methyl 5-fluoro-2-{4-[(1-morpholinyl)methyl]phenyl}benzofuran-7-carboxylate (compound 4j)

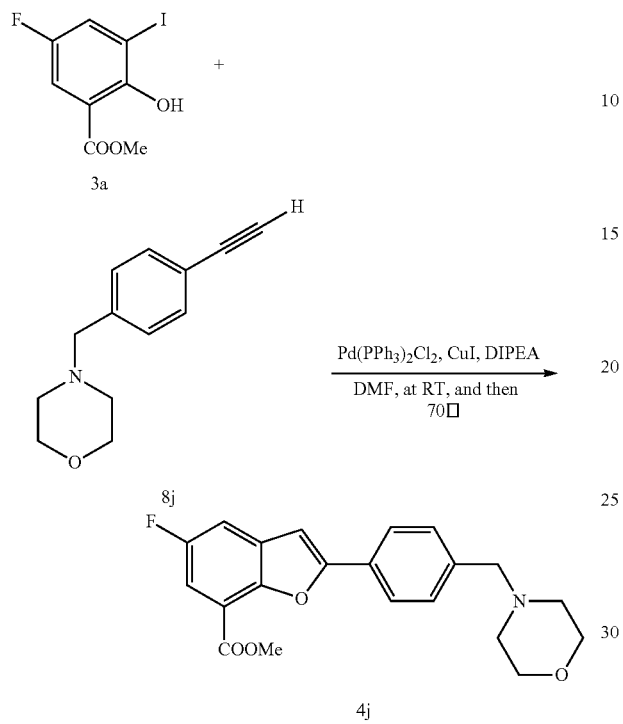

135 mg of brown oil with impurity was obtained according to the preparation process of compound 4a, wherein 113 mg (0.56 mmol) of 4-(4-ethynylbenzyl)morpholine (compound 8j) and 166 mg (0.56 mmol) of methyl 5-fluoro-3-iodosalicylate (compound 3a) were used as reactants.

MS (ESI) (M+H)+: m/z (%) 370.2 (100).

Preparation of 5-fluoro-2-{4-[(1-morpholinyl)methyl]phenyl}benzofuran-7-carboxamide (compound 5j)

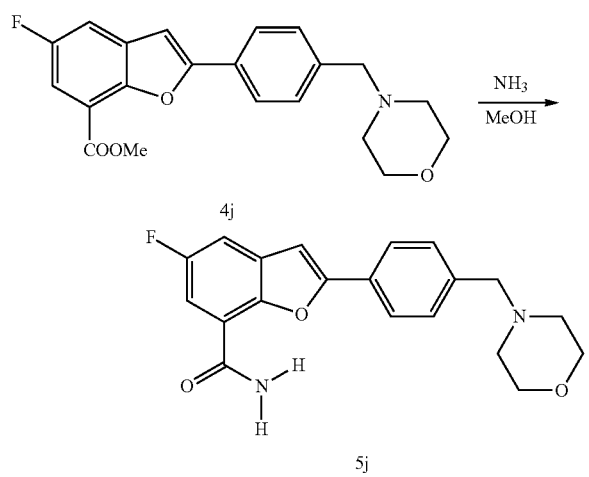

15 mg of white powder was obtained (9.2% yield for two steps) according to the preparation process of compound 5a, wherein 110 mg of methyl 5-fluoro-2-{4-[(1-morpholinyl)methyl]phenyl}benzofuran-7-carboxylate (compound 4j) with impurity was used as a reactant.

$^1$HNMR (300 MHz, CDCl$_3$) δ 7.80-7.68 (m, 3H), 7.47-7.33 (m, 4H), 7.05 (s, 1H), 6.31 (s, 1H), 3.73 (t, J=4.8 Hz, 4H), 3.56 (s, 2H), 2.47 (t, J=4.8 Hz, 4H); MS (ESI) (M+H)+: m/z (%) 355.2 (100).

Example 14

Preparation of 4-(4-ethynylbenzyl)thiomorpholine (compound 8k)

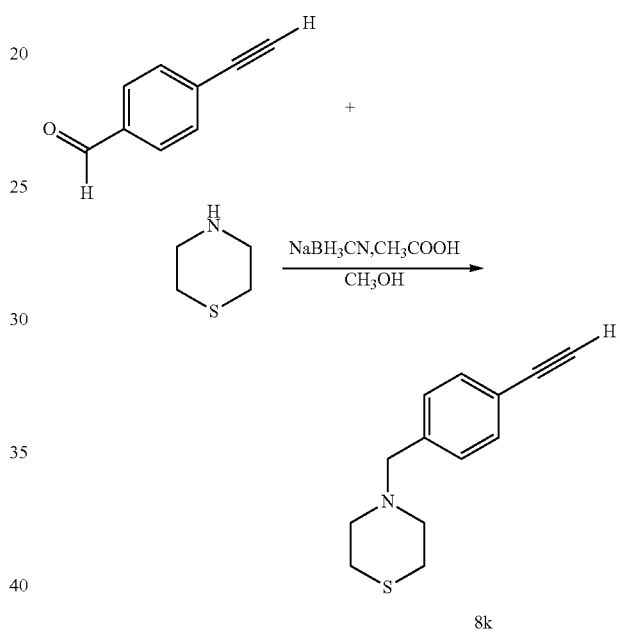

145 mg of yellow liquid was obtained in 56% yield according to the preparation process of compound 8f, wherein 156 mg (1.2 mmol) of 4-ethynylbenzaldehyde and 124 mg (1.2 mmol) of thiomorpholine were used as reactants.

$^1$HNMR (300 MHz, CDCl$_3$) δ 7.43 (d, J=8.1 Hz, 2H), 7.26 (d, J=8.1 Hz, 2H), 3.50 (s, 2H), 3.05 (s, 1H), 2.67 (br s, 8H); MS (ESI) (M+H)+: m/z (%) 218.1 (100).

Preparation of methyl 5-fluoro-2-{4-[(thiomorpholino)methyl]phenyl}benzofuran-7-carboxylate (compound 4k)

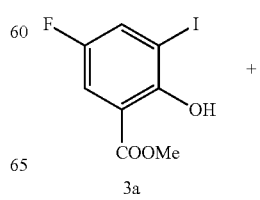

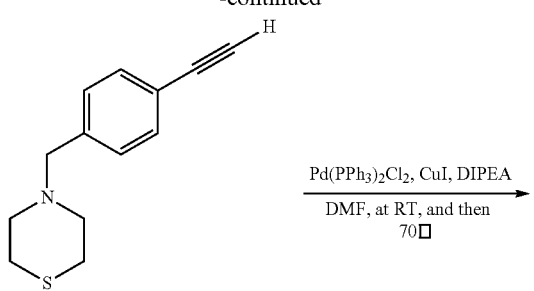

170 mg of brown oil with impurity was obtained according to the preparation process of compound 4a, wherein 120 mg (0.55 mmol) of 4-(4-ethynylbenzyl)thiomorpholine (compound 8k) and 164 mg (0.55 mmol) of methyl 5-fluoro-3-iodosalicylate (compound 3a) were used as reactants.

MS (ESI) (M+H)$^+$: m/z (%) 386.1 (100).

Preparation of 5-fluoro-2-{4-[(thiomorpholino)methyl]phenyl}benzofuran-7-carboxamide (compound 5k)

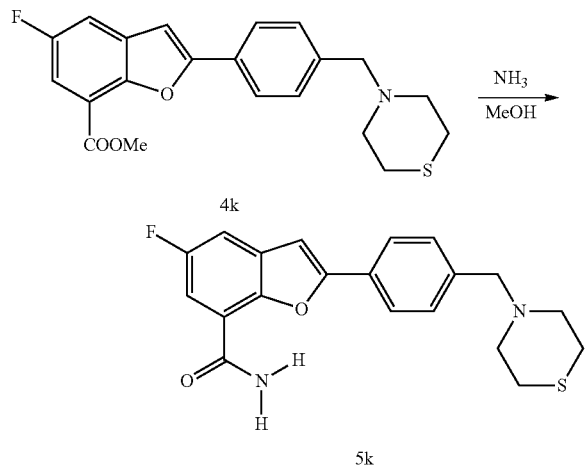

16 mg of white powder was obtained (9.2% yield for two steps) according to the preparation process of compound 5a, wherein 145 mg of methyl 5-fluoro-2-{4-[(thiomorpholino)methyl]phenyl}benzofuran-7-carboxylate (compound 4k) with impurity was used as a reactant.

$^1$HNMR (300 MHz, CDCl$_3$) δ 7.81-7.68 (m, 3H), 7.48-7.39 (m, 4H), 7.05 (s, 1H), 6.28 (br s, 1H), 3.57 (s, 2H), 2.74-2.68 (m, 8H); MS (ESI) (M+H)$^+$: m/z (%) 371.1 (100).

Example 15

Preparation of tert-butyl 4-[(4-acetylenylbenzyl)amino]-1-piperidyl carboxylate (compound 8l)

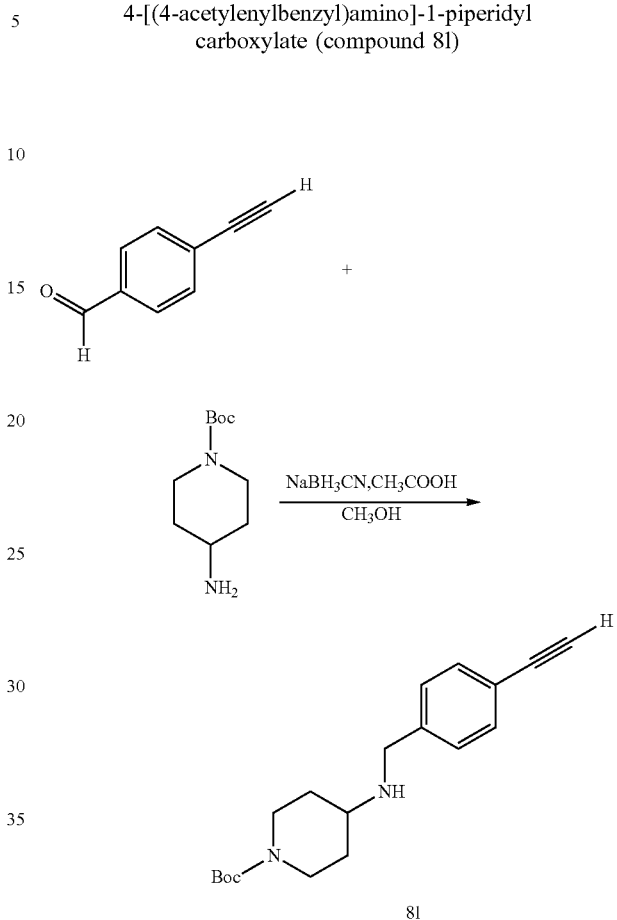

330 mg of yellow liquid was obtained in 85% yield according to the preparation process of compound 8f, wherein 156 mg (1.2 mmol) of 4-ethnylbenzaldehyde and 240 mg (1.2 mmol) of tert-butyl 4-amino-1-piperidyl carboxylate were used as reactants.

$^1$HNMR (300 MHz, CDCl$_3$) δ 7.44 (d, J=8.4 Hz, 2H), 7.26 (d, J=9.3 Hz, 2H), 4.00 (m, 2H), 3.82 (s, 2H), 3.05 (s, 1H), 2.79 (t, J=10.8 Hz, 2H), 2.64 (m, 1H), 1.83 (m, 2H), 1.45 (s, 9H), 1.28 (m, 2H); MS (ESI) (M+H)$^+$: m/z (%) 315.2 (54).

Preparation of tert-butyl 4-[4-(7-methoxycarbonyl-5-fluoro-2-benzofuranyl)benzylamino]-1-piperidyl carboxylate (compound 4l)

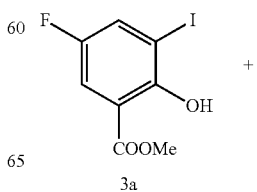

-continued

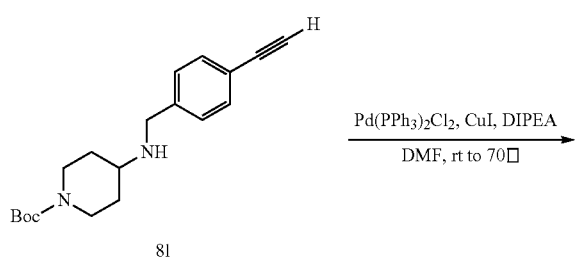

44 mg of brown oil with impurity was obtained according to the preparation process of compound 4a, wherein 181 mg (0.58 mmol) of tert-butyl 4-[(4-acetylenylbenzyl)amino]-1-piperidyl carboxylate (compound 8l) and 170 mg (0.58 mmol) of methyl 5-fluoro-3-iodosalicylate (compound 3a) were used as reactants.

MS (ESI) (M+H)$^+$: m/z (%) 483.3 (95).

Preparation of tert-butyl 4-[4-(7-carbamoyl-5-fluoro-2-benzofuranyl)benzylamino]-1-piperidyl carboxylate (compound 5la)

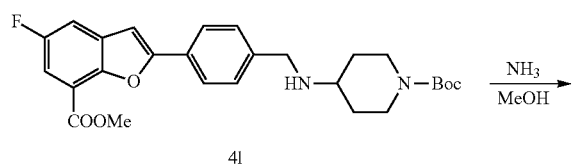

15 mg of white powder was obtained (8.1% yield for two steps) according to the preparation process of compound 5a, wherein 30 mg of tert-butyl 4-[4-(7-methoxycarbonyl-5-fluoro-2-benzofuranyl)benzylamino]-1-piperidyl carboxylate (compound 4l) with impurity was used as a reactant.

$^1$HNMR (300 MHz, CDCl$_3$) δ 7.79-7.74 (m, 3H), 7.46-7.38 (m, 4H), 7.04 (s, 1H), 6.31 (br s, 1H), 4.04 (br s, 2H), 3.89 (s, 2H), 2.81 (t, J=8.7 Hz, 2H), 2.70 (m, 1H), 1.88 (m, 2H), 1.45 (s, 9H), 1.32 (m, 2H); MS (ESI) (M−99)$^+$: m/z (%) 368.2 (100).

Preparation of 5-fluoro-2-{4-[(4-piperidyl)aminomethyl]phenyl}-benzofuran-7-carboxamide (compound 5l)

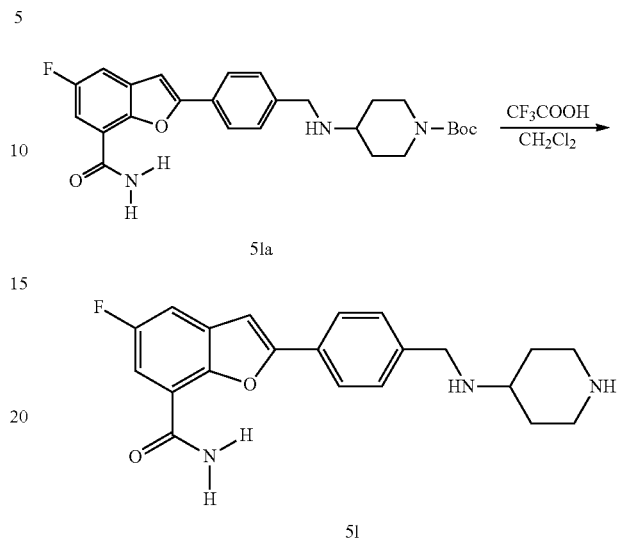

15 mg (0.03 mmol) of tert-butyl 4-[4-(7-carbamoyl-5-fluoro-2-benzofuranyl)benzylamino]-1-piperidyl carboxylate (compound 5la) was loaded into a 10 mL reaction bottle, and 2 mL dichloromethane and 0.5 mL trifluoroacetic acid were added. The reaction mixture was stirred for 2 hours at room temperature and the solvent was removed by rotary evaporator. Water was added and the pH value was adjusted to 10 by dilute sodium hydroxide solution. 50 mL of ethyl acetate was added for extraction and the organic layer was washed with 30 mL saturated sodium chloride solution, then dried on anhydrous sodium sulfate and evaporated to dryness by rotary evaporator. The residue was purified by column chromatography (silica gel, dichloromethane/methanol=10:1) to afford product 6 mg in 51% yield as white powder. $^1$HNMR (300 MHz, CDCl$_3$) δ 7.79-7.68 (m, 3H), 7.46-7.37 (m, 4H), 7.04 (s, 1H), 6.52 (br s, 1H), 3.88 (s, 2H), 3.11 (m, 2H), 2.61 (m, 3H), 1.92 (m, 2H), 1.32 (br s, 2H); MS (ESI) (M+H)$^+$: m/z (%) 368.2 (100).

Example 16

Preparation of (R)—N-(4-ethynylbenzyl)tetrahydrofuran-3-amine (compound 8m)

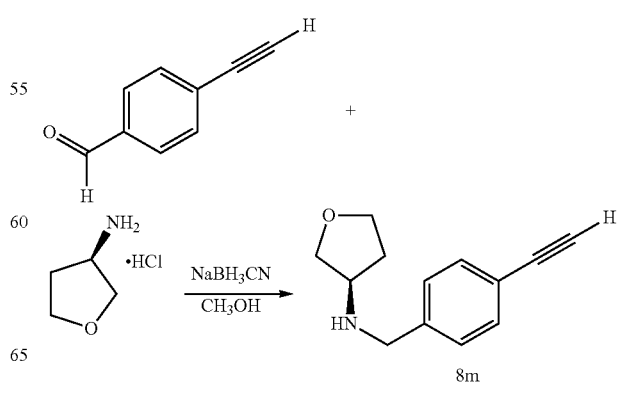

108 mg of yellow oil was obtained in 54% yield according to the preparation process in example 4, wherein 130 mg (1 mmol) of 4-ethynylbenzaldehyde and 124 mg (1 mmol) of (R)-3-aminotetrahydrofuran were used as reactants.

$^1$HNMR (300 MHz, CDCl$_3$) δ 7.44 (d, J=6.0 Hz, 2H)+, 7.28 (d, J=6.0 Hz, 2H), 3.92 (m, 1H), 3.81-3.74 (s, 4H), 3.61 (m, 1H), 3.41 (m, 1H), 3.06 (s, 1H), 2.10 (m, 1H), 1.74 (m, 1H); MS (ESI) (M+H)$^+$: m/z (%) 202.1 (95).

Preparation of methyl (R)-5-fluoro-2-{4-[(3-tetrahydrofurylamino)methyl]phenyl}-benzofuran-7-carboxylate (compound 4m)

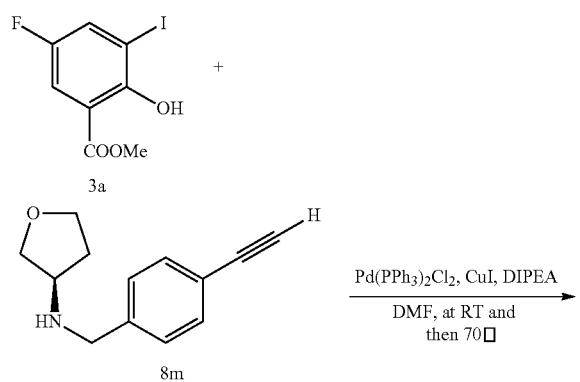

100 mg of brown oil with impurity was obtained according to the preparation process of compound 4a, wherein 98 mg (0.49 mmol) of (R)—N-(4-ethynylbenzyl)tetrahydrofuran-3-amine (compound 8m) and 144 mg (0.49 mmol) of methyl 5-fluoro-3-iodosalicylate (compound 3a) were used as reactants.

MS (ESI) (M+H)$^+$: m/z (%) 370.2 (95).

Preparation of (R)-5-fluoro-2-{4-[(3-tetrahydrofurylamino)methyl]phenyl}benzofuran-7-carboxamide (compound 5m)

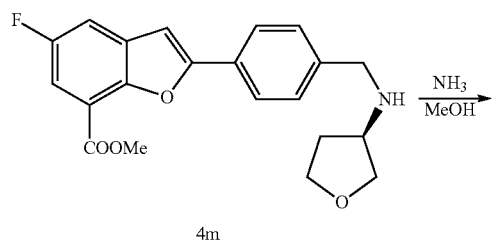

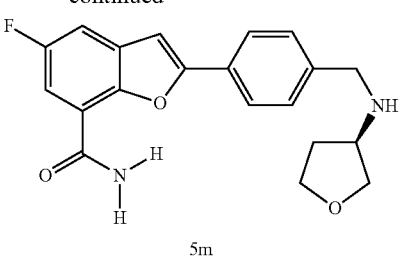

7 mg of white powder was obtained (4.5% yield for two steps) according to the preparation process of compound 5a, wherein 90 mg of methyl (R)-5-fluoro-2-{4-[(3-tetrahydrofurylamino)methyl]phenyl}benzofuran-7-carboxylate (compound 4m) with impurity was used as a reactant.

$^1$HNMR (300 MHz, CDCl$_3$) δ 7.80-7.74 (m, 3H), 7.45 (d, J=8.4 Hz, 2H), 7.40 (m, 2H), 7.04 (s, 1H), 6.37 (s, 1H), 4.00-3.92 (m, 1H), 3.85-3.75 (m, 4H), 3.69-3.64 (m, 1H), 3.50-3.43 (m, 1H), 2.20-2.08 (m, 1H), 1.85-1.78 (m, 1H); MS (ESI) (M+H)$^+$: m/z (%) 355.2 (100).

Example 17

Preparation of N-(4-ethynylbenzyl)cyclopropylamine (compound 8n)

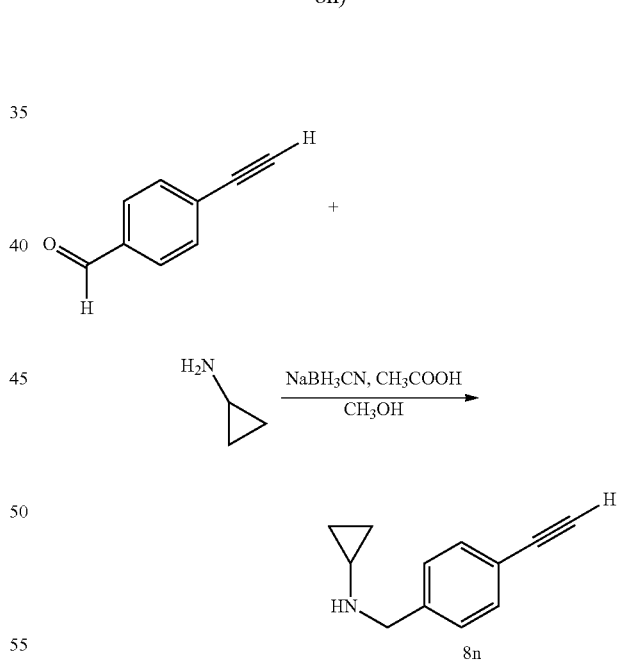

272 mg of colourless liquid was obtained in 79% yield according to the preparation process of compound 8f, wherein 253 mg (1.95 mmol) of 4-ethynylbenzaldehyde and 111 mg (1.95 mmol) of cyclopropylamine were used as reactants.

$^1$HNMR (300 MHz, CDCl$_3$) δ 7.44 (d, J=8.1 Hz, 2H), 7.26 (d, J=8.1 Hz, 2H), 3.83 (s, 2H), 3.05 (s, 1H), 2.16-2.09 (m, 1H), 0.46-0.33 (m, 4H) MS (ESI) (M+H)$^+$: m/z (%) 172.2 (30).

Preparation of methyl 5-fluoro-2-[4-(cyclopropy-laminomethyl)phenyl]benzofuran-7-carboxylate (compound 4n)

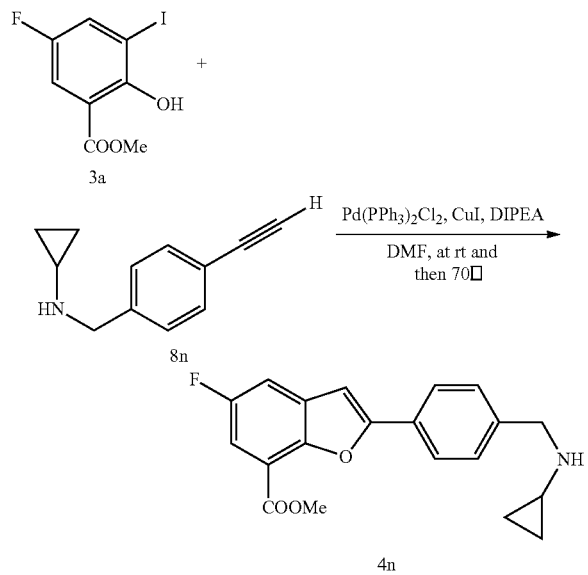

95 mg of brown oil with impurity was obtained according to the preparation process of compound 4a, wherein 83 mg (0.49 mmol) of N-(4-ethynylbenzyl)cyclopropylamine (compound 8n) and 144 mg (0.49 mmol) of methyl 5-fluoro-3-iodosalicylate (compound 3a) were used as reactants.

MS (ESI) (M+H)$^+$: m/z (%) 340.2 (60).

Preparation of 5-fluoro-2-[4-(cyclopropylaminomethyl)phenyl]benzofuran-7-carboxamide (compound 5n)

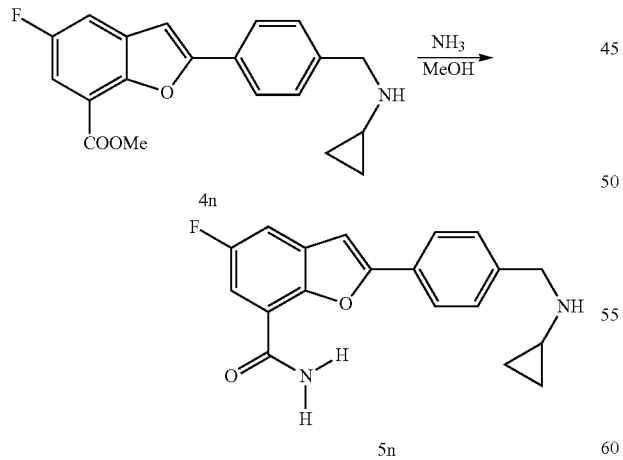

12 mg of white powder was obtained (7.6% yield for two steps) according to the preparation process of compound 5a, wherein 95 mg of methyl 5-fluoro-2-[4-(cyclopropylaminomethyl)phenyl]benzofuran-7-carboxylate (compound 4n) with impurity was used as a reactant.

$^1$HNMR (300 MHz, CDCl$_3$/CD$_3$OD) δ 7.75-7.68 (m, 3H), 7.41-7.35 (m, 3H), 7.02 (s, 1H), 3.84 (s, 2H), 2.16-2.09 (m, 1H), 0.48-0.35 (m, 4H); MS (ESI) (M+H)$^+$: m/z (%) 325.2 (52).

Example 18

Preparation of N-(4-ethynylbenzyl)isopropylamine (compound 8o)

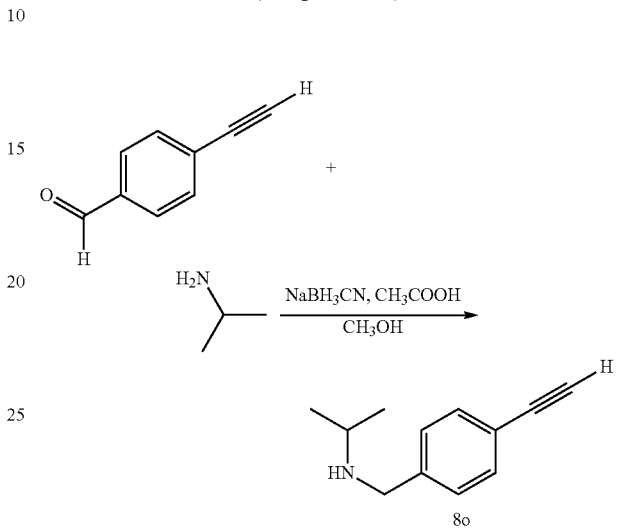

272 mg of colourless liquid was obtained in 79% yield according to the preparation process of compound 8f, wherein 260 mg (2 mmol) of 4-ethynylbenzaldehyde and 120 mg (2 mmol) of isopropylamine were used as reactants.

$^1$HNMR (300 MHz, CDCl$_3$) δ 7.43 (d, J=8.4 Hz, 2H), 7.26 (d, J=8.4 Hz, 2H), 3.77 (s, 2H), 3.04 (s, 1H), 2.89-2.78 (m, 1H), 1.08 (d, J=6.3 Hz, 6H); MS (ESI) (M+H)$^+$: m/z (%) 174.2 (73).

Preparation of methyl 5-fluoro-2-[4-(isopropylaminomethyl)phenyl]benzofuran-7-carboxylate (compound 4o)

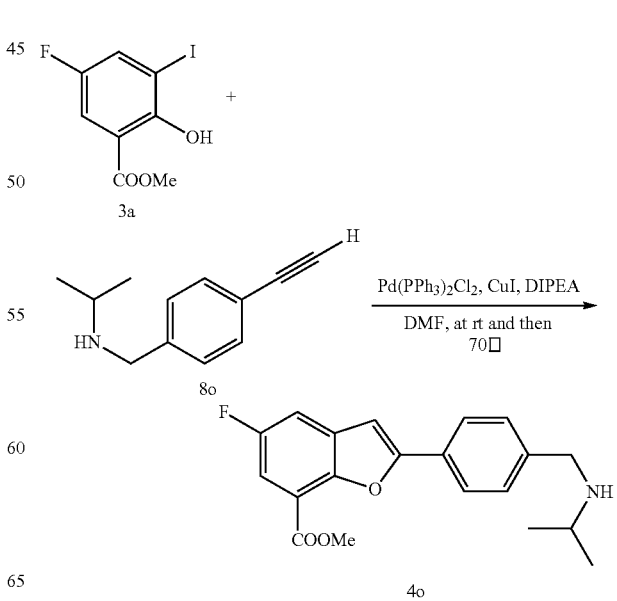

165 mg of brown oil with impurity was obtained according to the preparation process of compound 4a, wherein 110 mg (0.63 mmol) of N-(4-ethynylbenzyl)isopropylamine (compound 8o) and 188 mg (0.63 mmol) of methyl 5-fluoro-3-iodosalicylate (compound 3a) were used as reactants.

MS (ESI) (M+H)+: m/z (%) 342.2 (100).

Preparation of 5-fluoro-2-[4-(isopropylaminomethyl)phenyl]benzofuran-7-carboxamide (compound 5o)

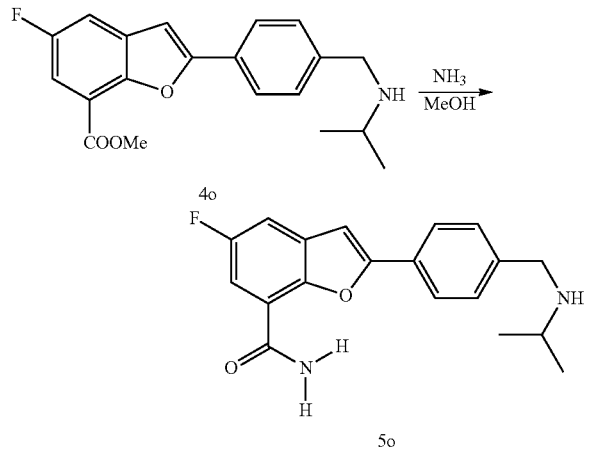

13 mg of white solid was obtained (6% yield for two steps) according to the preparation process of compound 5a, wherein 160 mg of methyl 5-fluoro-2-[4-(isopropylaminomethyl) phenyl]benzofuran-7-carboxylate (compound 4o) with impurity was used as a reactant.

$^1$HNMR (300 MHz, CDCl$_3$) δ 7.74-7.72 (m, 3H), 7.43-7.35 (m, 4H), 7.02 (s, 1H), 6.36 (s, 1H), 3.82 (s, 2H), 2.85 (m, 1H), 1.09 (d, J=6.3Hz, 6H); MS (ESI) (M+H)+: m/z (%) 327. (100).

Example 19

Preparation of 4-[(trimethylsilyl)acetylenyl]-3-fluorobenzaldehyde (compound 13d)

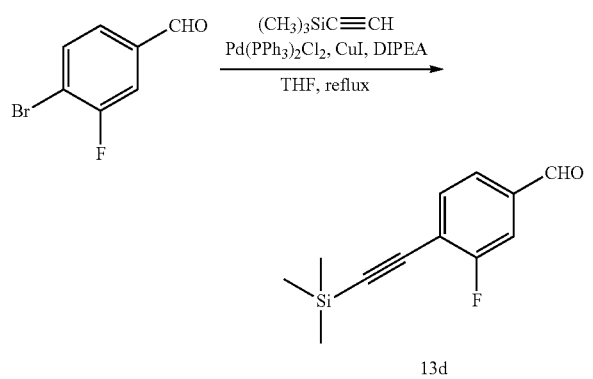

102 mg of yellow solid was obtained in 92% yield according to the preparation process of compound 11a, wherein 101 mg (0.5 mmol) of 3-fluoro-4-bromobenzaldehyde was used as a reactant.

$^1$HNMR (300 MHz, CDCl$_3$) δ 9.96 (d, J=1.2, 1H), 7.61-7.54 (m, 3H), 0.28 (s, 9H); MS (ESI) (M+H)+: m/z (%) 221.1 (100).

Preparation of 4-acetylenyl-3-fluorobenzaldehyde (compound 14d)

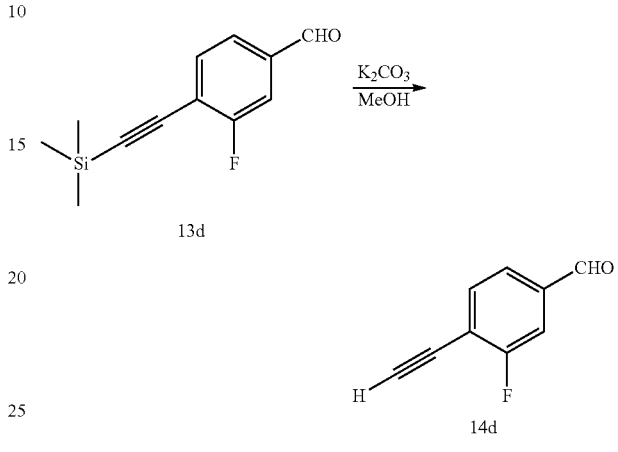

260 mg of white flocculent solid was obtained in 88% yield according to the preparation process of compound 8a, wherein 440 mg (2 mmol) of 4-[(trimethylsilyl)acetylenyl]-3-fluorobenzaldehyde (compound 13d) was used as a reactant.

$^1$HNMR (300 MHz, CDCl$_3$) δ 9.97 (s, 1H), 7.68-7.57 (m, 3H), 3.57 (s, 1H); MS (ESI) (M+H)+: m/z (%) 149.1 (10).

Preparation of N-methyl-1-(4-ethynyl-3-fluorophenyl)methylamine (compound 8p)

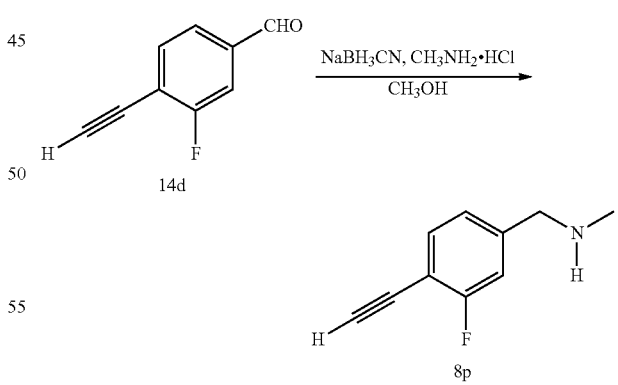

182 mg of yellow oil was obtained in 74% yield according to the preparation process in example 4, wherein 222 mg (1.5 mmol) of 4-ethynyl-3-fluorobenzaldehyde (compound 14d) was used as a reactant.

$^1$HNMR (300 MHz, CDCl$_3$) δ 7.42 (d, J=7.8 Hz, 1H), 7.09-7.04 (m, 2H), 3.74 (s, 2H), 3.27 (s, 1H), 2.43 (s, 3H); MS (ESI) (M+H)+: m/z (%) 164.1 (26).

Preparation of methyl 5-fluoro-2-{4-[(methylamino)methyl]-2-fluorophenyl}benzofuran-7-carboxylate (compound 4p)

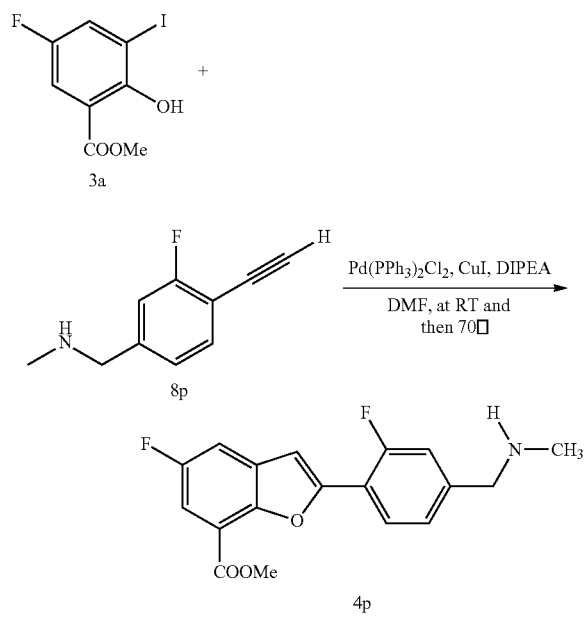

15 mg of brown powder was obtained in 9% yield according to the preparation process of compound 4a, wherein 82 mg (0.50 mmol) of N-methyl-1-(4-acetylenyl-3-fluorophenyl)methylamine (compound 8p) and 148 mg (0.50 mmol) of methyl 5-fluoro-3-iodosalicylate (compound 3a) were used as reactants.

$^1$HNMR (300 MHz, CDCl$_3$) δ 8.05 (t, J=7.8 Hz, 1H), 7.64 (dd, J=2.7, 9.3 Hz, 1H), 7.44 (dd, J=2.7, 8.1 Hz, 1H), 7.24-7.12 (m, 3H), 4.04 (s, 3H), 3.80 (s, 2H), 2.47 (s, 3H); MS (ESI) (M+H)$^+$: m/z (%) 332.1 (10).

Preparation of 5-fluoro-2-{4-[(methylamino)methyl]-2-fluorophenyl}benzofuran-7-carboxamide (compound 5p)

6 mg of light brown powder was obtained in 63% yield according to the preparation process of compound 5a, wherein 10 mg (0.03 mmol) of methyl 5-fluoro-2-{4-[(methylamino)methyl]-2-fluorophenyl}benzofuran-7-carboxylate (compound 4p) was used as a reactant.

$^1$HNMR (300 MHz, CD$_3$OD) δ 8.03 (t, J=7.9 Hz, 1H), 7.55 (m, 2H), 7.34-7.24 (m, 3H), 3.77 (s, 2H), 2.40 (s, 3H; MS (ESI) (M+H)$^+$: m/z (%) 317.2 (50).

Example 20

Preparation of 5-fluoro-2-{4-[(dimethylamino)methyl]phenyl}benzofuran-7-carboxamide hydrochloride 937 mg (3 mmol) of 5-fluoro-2-{4-[(dimethylamino)methyl]phenyl}benzofuran-7-carboxamide (compound 5a) was added into a 250 mL flask, then methanol was added as the solvent and the mixture was stirred at room temperature to dissolve the compound. 235.5 mg (3 mmol) of acetylchloride was added dropwise and stirred for half an hour. 1.02 g of white powder was obtained after the solvent was removed by rotary evaporation in 98% yield. Melting point: 232-234 □.

$^1$HNMR (300 MHz, d$_6$-DMSO) δ 10.96 (br s, 1H), 8.09 (d, J=8.1 Hz, 2H), 7.95 (s, 1H), 7.91 (s, 1H), 7.76-7.68 (m, 3H), 7.61 (s, 1H), 7.50 (dd, J=2.4, 9.9Hz, 1H), 4.33 (d, J=5.4Hz, 2H), 2.70 (d, J=4.8Hz, 6H).

Example 21

Preparation of 5-fluoro-2-{4-[(methylamino)methyl]phenyl}benzofuran-7-carboxamide hydrochloride

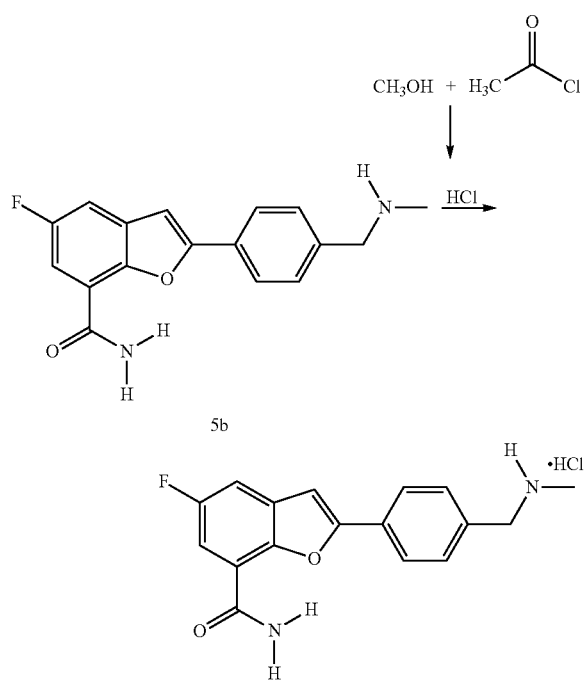

Methanol was added to 298 mg (1 mmol) of 5-fluoro-2-{4-[(methylamino)methyl]phenyl}benzofuran-7-carboxamide (compound 5b) and the mixture was stirred at room temperature to dissolve the compound. 78.5 mg (1 mmol) of acetylchloride was added dropwise and stirred for half an hour. 330 mg of beige powder was obtained after the solvent was removed by rotary evaporation in 98% yield. Melting point: 286-288 □.

$^1$HNMR (300 MHz, $d_6$-DMSO) δ 9.42 (br s, 2H), 8.07 (d, J=8.1 Hz, 2H), 7.94 (s, 1H), 7.91 (s, 1H), 7.72-7.67 (m, 3H), 7.59 (s, 1H), 7.50 (dd, J=2.7, 9.9 Hz, 1H), 4.17 (t, J=5.4 Hz, 2H), 2.70 (d, J=5.1 Hz, 3H).

Experimental Example 1

Experiments of PARP1 Enzymatic Inhibition at Molecular Levels

Experimental method: Enzyme-Linked Immunosorbent Assays (ELISA) (see enzyme-Linked Immunosorbent Assay reported by Decker P.; reference: Decker P, Miranda E A, de Murcia G, Muller S. An improved nonisotopic test to screen a large series of new inhibitor molecules of Poly(ADP-ribose) Polymerase activity for therapeutic applications. Clinical Cancer Research, 5: 1169-1172, 1999.), the principle of which is that the substrate histone is coated on absorptive 96 well plates, and the recombination enzyme PARP1, the substrate $NAD^+$ and the activated DNA are added to make the PARP1 enzyme reaction occur thereby generating the product PAR (poly(ADP-ribose)) on histone; and then the anti-PAR antibody is added, and the intensity of the product PAR in histone coated on 96 well plates is measured to reflect the enzymatic activity of PARP.

The specific method was as follows:

1. Histone is a well-known important substrate of PARP1. Histone was coated on 96 well elisa plate using potassium-ion-free PBS (10 mM sodium phosphate buffer, 150 mM NaCl, pH 7.2-7.4). The plate was placed in a shaking incubator at 37° C. overnight and then the liquid in the well was removed. The plate was washed with T-PBS (PBS containing 0.1% Tween-20, 120 μL/well) for five times and dried in an oven at 37° C.

2. $NAD^+$ (final concentration: 8 μM/well), DNA (100 ng/well), and PARP1 (10 ng/well) (diluted with the PARP1 reaction buffer containing 50 mM Tris (trimethylol aminomethane), 2 mM $MgCl_2$, pH 8.0) were added. Ten μL of the tested compounds (the positive control compound AZD2281 with the tradename Olaparib, purchased from LC Laboratories) with certain diluted concentrations (from 10 μM down, 10-fold dilution, and 6 gradients) was added to each well in duplicate. The reaction system was set to 100 μL/well (supplemented by foregoing PARP1 reaction buffer) and placed into a shaker at 37° C. overnight. The blank, positive and negative controls were set, wherein the wells without the enzyme were set as blank controls, the wells without the tested compounds were set as negative controls and the wells with the positive control inhibitor were set as positive controls. The reaction was initiated and carried out for 1 hour at 37° C. in a shaking incubator.

3. The plate was washed with PBS-T for three times. The primary antibody, anti-PAR MAb10H (1:4000, diluted with PBS-T containing 5 μg/mL BSA) was added (100 μL/well) and incubated in a shaking incubator at 37° C. for 1 hour.

4. The plate was washed with PBS-T for three times. The second antibody labeled with peroxidase (anti-mouse antibody) (1:2000, diluted with PBS-T containing 5 μg/mL BSA) was added (100 μL/well) and reacted for 30 minutes in a shaking incubator at 37° C.

5. 2 mg/mL of the 0-phenylenediamine dihydrochloride (OPD) color development liquid was added (100 μL/well) [diluted with 0.1 M citric acid-sodium citrate buffer (pH=5.4) containing 0.03% of $H_2O_2$] and reacted for 15 minutes in darkness. (The ultrasonic treatment is necessary to dissolve OPD and the color development liquid should be prepared just before use)

6. 2 M $H_2SO_4$ (50 μL/well) was used to quench the reaction. A Molecular Devices microplate reader [purchased from Molecular Devices (MDC), SpectraMax 190 Microplate Reader (90V to 240V)] was used to record OD values at 490-nm wavelength.

The inhibiting of the medicament on the PARP enzymatic activity was calculated according to the following equation:

Inhibition ratio (%)=(OD of control wells−OD of treatment wells)/OD of control wells×100%

The concentration of the medicaments corresponding to the 50% inhibition ratio, i.e. $IC_{50}$, was calculated with the Logit method based on the above calculation results. The experiments were repeated for three times, from which the mean and the standard deviation were calculated.

Experimental Example 2

Experiments of In Vitro Cell Proliferation Inhibition

Cell lines: Chinese hamster lung fibroblast cell line VC8 ($BRCA2^{-/-}$) and wild type cell line V79 (given as a gift by Professor Malgorzata Z. Zdzienicka, Leiden University, Holland)

Experimental method: MTT assays (see MTT assay reported by Mosman T., reference: Mosmann T. Rapid colorimetric assay for cellular growth and survival application to proliferation and cytotoxicity assays. Journal of Immunological Methods 65 (1-2): 55-63, 1983.). The full name of MTT is 3-(4,5-dimethylthiazol-2-yl)-2,5-diphenyltetrazolium bromide. The principle of MTT assays is that succinodehydrogenase in mitochondria in living cells can reduce exogenous MTT to violet crystal formazan which is insoluble in water and precipitates in the cell, while the dead cell does not have such function. Within a certain number of cells, the amount of formed crystal formazan will be proportional to the number of cells. Formazan can be dissolved in the mixed solution of SDS, isobutanol and HCl, and the OD value at 570-nm wavelength can be detected with an enzyme-linked immunometric meter to reflect indirectly the amount of living cells, thereby calculating the cell inhibition ratio.

The specific method was as follows. The cells in logarithmic growth phase were inoculated in 96-well plate, with 2000 V79 cells/well and 4000 VC8 cells/well, 100 μL/well, and cultured overnight. Different concentrations (from 10 μM down, 5-fold dilution and 6 gradients) of medicaments in triplicate were added and incubated for 72 h, and the corresponding concentration of normal saline control wells and zero setting wells without cells were also set. After the incubation was finished, 20 μL MTT (5 mg/mL) was added and cultured for 4 h at 37° C. 100 μL of mixed solution (10% SDS-5% isobutanol-0.01 M HCl) was added and the plate was placed at 37° C. overnight. OD values at 570 nm wavelength were measured. The inhibition degree of the medicament on cell proliferation was calculated according to the following equation:

Inhibition ratio (%)=(OD of control wells−OD of treatment wells)/OD of control wells×100%

The concentration of the medicaments corresponding to the 50% inhibition ratio, i.e. $IC_{50}$, was calculated with the Logit method based on the above calculation results. The experiments were repeated for three times, from which the mean and the standard deviation were calculated.

The results of the biological activity of preferred compounds in the present invention at molecular levels and cellular levels were shown in Table 2.

TABLE 2

The activity of the preferred compounds at molecular and cellular levels

| No. | ELISA $IC_{50}$ (nM) | | | VC8 cell $IC_{50}$ (μM) | | | V79 cell $IC_{50}$ (μM) | |
|---|---|---|---|---|---|---|---|---|
| AZD 2281 | 8.9 ± 6.3 | | | 0.82 ± 0.33 | | | >10 | |
| 5a | 11.8 ± 8.9 | | | 0.75 ± 0.10 | | | >10 | |
| 5b | 44.8 ± 12.5 | | | 0.59 ± 0.15 | | | >10 | |
| 7a | | 9254 | | | / | | | |
| 5c | 37 | 34.2 | 72 | 6.608 | 2.920 | >10 | >10 | |
| 5d | 23 | 27.9 | 58 | 3.270 | 1.738 | >10 | >10 | |
| 5e | 14.8 | 20.8 | 74 | 2.084 | 1.507 | >10 | >10 | |
| 5f | 4.6 | 17.6 | 147 | 3.359 | 2.624 | >10 | >10 | |
| 5g | 83 | 104.6 | 187 | 2.079 | 2.144 | >10 | >10 | |
| 5h | 1.3 | 3.1 | 114 | 2.598 | 2.006 | >10 | >10 | |
| 5i | 104 | 101 | 207 | >10 | 2.109 | >10 | >10 | |
| 5j | 2.96 | 7.9 | 339 | 2.811 | 7.391 | >10 | >10 | |
| 5k | 1059 | 2062 | 1521 | >10 | >10 | >10 | >10 | |
| 5l | 182 | 107 | 393 | 8.306 | 8.216 | >10 | >10 | |
| 5m | 49 | 9.5 | 17 | 1.151 | 1.179 | >10 | >10 | |
| 5n | 18 | 31 | 73 | 1.867 | 0.903 | >10 | >10 | |
| 5o | 32 | 18.8 | 25 | 1.092 | 0.941 | >10 | >10 | |
| 5p | 22 | 8.9 | 40 | 1.361 | 1.617 | >10 | >10 | |

It can be seen from Table 2 that the compounds in the present invention have excellent inhibitory activities on PARP1. The inhibitory activity at molecular levels is of the same order of magnitude with that of the positive control group. The experiment of in vitro cell proliferation inhibition shows that the compounds in the present invention have excellent inhibitory activities on the Chinese hamster lung fibroblast cell line VC8 (BRCA2$^{-/-}$), while 50% inhibiting concentrations thereof for the wild-type Chinese hamster lung cell line V79 are higher than 10 μM, suggesting that designed compounds have high selectivity for BRCA-deficient cells and the test results match the mechanism of action thereof.

Experimental Example 3

Experiments of enzymatic inhibition on the PARP family members at molecular levels.

Experimental method: Enzyme-Linked Immunosorbent Assays (ELISA), the principle of which is that the substrate histone is coated on absorptive 96 well plates, and the recombination enzyme PARP, the substrate NAD$^+$ and the activating DNA are added to make the PARP enzyme reaction occur thereby generating the product PAR (poly (ADP-ribose)) on histone; and then the anti-PAR antibody is added, and the intensity of the product PAR in histone coated on 96 well plates is measured to reflect the enzymatic activity of PARP.

The specific method was as follows:

1. The substrate histone for enzyme reaction was coated on 96-well ELISA plates using potassium-ion-free PBS (10 mM sodium phosphate buffer, 150 mM NaCl, pH 7.2-7.4). The plate was placed in a shaking incubator at 37° C. overnight and then the liquid in the well was removed. The plate was washed with T-PBS (PBS containing 0.1% Tween-20, 120 μL/well) for five times and dried in an oven at 37° C.

2. 50 μL of reaction buffer (Tris.HCl, pH 8.0) containing NAD$^+$ (2.5 μM), biotinylated NAD$^+$), activated DNA (100 ng/well), a PARP enzyme (details can be found in Table 4) and the test compounds with certain diluted concentrations (final concentration: 0.3 nM-10 μM) were added in duplicate. The reaction was carried out at room temperature for 1 hour (the reaction temperature of TNKS was 30° C.). The blank, positive and negative controls were also set.

3. After enzymatic reactions, the plate was washed with PBS for three times. 50 μL of Streptavidin-horseradish peroxidase (Strep-HRP) was added to each well and the plate was incubated at room temperature for an additional 30 minutes.

4. 100 μl of developer reagents were added to wells and luminescence was measured using a BioTek Synergy™ 2 microplate reader. The inhibition of the tested compounds on the PARP emzymatic activity was calculated according to the following equation:

Inhibition ratio (%)=(OD of control wells−OD of treatment wells)/OD of control wells×100%

The concentration of the tested compounds corresponding to the 50% inhibition ratio, i.e. $IC_{50}$, was calculated with the Logit method based on the above calculation results. The experiments were repeated for three times, from which the mean and the standard deviation were calculated.

The in vitro inhibition of compound 5b on six major isoenzymes from the PARP family at molecular levels was shown in Table 3.

TABLE 3 the results of inhibition effects of compound 5b on the PARP family members

| PARPs | IC$_{50}$ | |
|---|---|---|
| | 5b | AZD2281 |
| PARP1 | 3.2 nM | 1.1 nM |
| PARP2 | 1.9 nM | 0.9 nM |
| PARP3 | >10 μM | 258 nM |
| TNKS1 | 1.6 μM | 14.5 nM |
| TNKS2 | 1.3 μM | 5.9 nM |
| PARP6 | >10 μM | 1.5 μM |

It can be seen from table 3 that compared with the positive control AZD2281, compound 5b in the present invention showed relatively weak inhibitory activity on the subtype enzymes except PARP1/2. The inhibitory activity of compound 5b on PARP1/2 was at least 400 times of that on other isoenzymes in the family. The results indicated that compound 5b had high selectivity for PARP1/2 and was a high-selectivity inhibitor for PARP1/2. The selectivity of compound 5b for other subtypes was better than those of the positive control AZD2281.

TABLE 4

The concentration of the substrate and enzyme used in ELISA

| experiment | Enzyme used in the reaction | substrate activated DNA |
|---|---|---|
| PARP1 | 15 ng | 2.5 μM NAD$^+$/2.5 μM NAD$^+$-biotin 0.026 mg/mL |
| PARP2 | 27 ng | 2.5 μM NAD$^+$/2.5 μM NAD$^+$-biotin 0.026 mg/mL |
| PARP3 | 75 ng | 25 μM NAD$^+$/2.5 μM NAD$^+$-biotin 0.026 mg/mL |
| TNKS1 | 40 ng | 25 μM NAD$^+$/2.5 μM NAD$^+$-biotin N/A |
| TNKS2 | 15 ng | 25 μM NAD$^+$/2.5 μM NAD$^+$-biotin N/A |
| PARP6 | 600 ng | 50 μM NAD$^+$/2.5 μM NAD$^+$-biotin 0.026 mg/mL |

The preliminary pharmacokinetic experiment for preferred compound 5b was carried out in the present invention, and the method and results are as follows.

1. Administration Method

Healthy SD rats (supplied by Shanghai Sippr-BK Lab. Animal Co. Ltd, the Production License Number for the experimental animals: SCXK (hu), 200-220 g of weight, male) were divided into groups randomly and administrated by gavage, respectively. The compound was dissolved in normal saline.

The rats fasted for 12 h and could drink water ad libitum before experiment. 2 h after dosing, the rats were provided with food all together.

The time point for collecting blood samples and the sample processing are listed as follows.

Intragastric administration: 0.25, 0.5, 1.0, 2.0, 3.0, 5.0, 7.0, 9.0 and 24 h after administration: 0.3 mL venous blood was taken from retrobulbar venous plexus of the rat and loaded into heparinization tubes. After being centrifuged at 11000 rpm for 5 min, the plasma was separated and frozen at −20° C. in a refrigerator.

2. Experiment Results

After 10 mg/kg of compound 5b was administrated by gavage, the time to the peak of plasma concentration (Tmax) was 3.5±2.4 h, the achieved peak concentration (Cmax) was 92.5±33.2 ng/mL, the area under the plasma concentration-time curve (AUC$_{0-t}$) was 452±103 ng·h/mL, elimination half life ($t_{1/2}$) was 1.75±0.94 h, and mean residue time (MRT) was 3.94±1.13 h. After 10 mg/kg of compound 5b was administrated to the rats by gavage, the absolute bioavailability was 58.9%.

TABLE 5 the pharmacokinetic parameters after 10 mg/kg of compound 5b was administrated to the rats by gavage

| Animal No. | T$_{max}$ (h) | C$_{max}$ (ng/mL) | AUC$_{0-t}$ (ng · h/mL) | AUC$_{0-\infty}$ (ng · h/mL) | MRT (h) | t$_{1/2}$ (h) | F (%) |
|---|---|---|---|---|---|---|---|
| 8 | 2.0 | 109 | 587 | 595 | 3.34 | 1.30 | |
| 9 | 7.0 | 52.0 | 352 | 407 | 5.57 | 3.14 | |
| 10 | 2.0 | 128 | 474 | 478 | 3.04 | 1.07 | |
| 11 | 3.0 | 81.1 | 394 | 404 | 3.82 | 1.48 | |
| Average | 3.5 | 92.5 | 452 | 471 | 3.94 | 1.75 | 58.9 |
| standard deviation | 2.4 | 33.2 | 103 | 90 | 1.13 | 0.94 | |
| CV (%) | 68.0 | 35.9 | 22.8 | 19.0 | 28.7 | 53.9 | |

3. Analysis of Results

The preliminary pharmacokinetic experiment results showed a moderate eliminate rate of compound 5b in vivo and high bioavailability. After 10 mg/kg of 5b was administrated to rats by gavage, the absolute bioavailability was 58.9%, and the compound exhibited good absorption, distribution, and metabolism in vivo, while the oral bioavailability of rats during phase II clinical trials for compound AZD2281 was only 11.1%.

The invention claimed is:

1. A 2-aryl-benzofuran-7-carboxamide compound as shown in formula I or a pharmacologically or physiologically acceptable salt thereof,

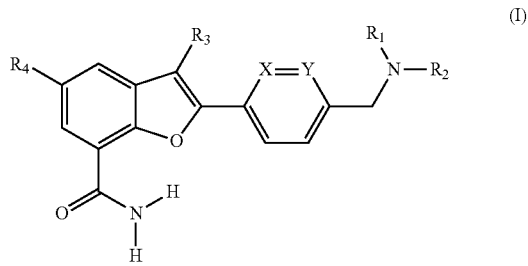

wherein,
each of $R_1$ and $R_2$ is independently H, a straight or branched $C_1$-$C_4$ alkyl, a $C_3$-$C_4$ cycloalkyl or a saturated 5- or 6-membered heterocyclic group containing O or N;

or $R_1$ and $R_2$ together with N form an unsubstituted or substituted saturated 5- or 6-membered heterocyclic group containing at least one heteroatom, wherein the heteroatom of the heterocyclic group is O, N and S, and the substituent, if present, is a methyl on N;

$R_3$ is a hydrogen atom or a chlorine atom;
$R_4$ is a hydrogen atom or a fluorine atom;
X is CH, CF or N; and
Y is CH, CF or N.

2. The compound or the pharmacologically or physiologically acceptable salt thereof according to claim 1, wherein $R_1$ is H, a methyl, an ethyl, an isopropyl, a cyclopropyl, a piperidin-4-yl or (R)tetrahydrofuran-3-yl;

R₂ is H, a methyl, an ethyl, an isopropyl, a cyclopropyl, a piperidin-4-yl or (R)tetrahydrofuran-3-yl;
or R₁ and R₂ together with N form an unsubstituted or substituted morpholinyl, piperazinyl, thiomorpholinyl, piperidinyl or pyrrolidinyl, wherein the substituent is a methyl on N;
R₃ is a hydrogen atom;
R₄ is a fluorine atom;
X is CH, CF or N; and
Y is CH, CF or N.

3. The compound or the pharmacologically or physiologically acceptable salt thereof according to claim 2, wherein, R₁ is H or a methyl;

R₂ is a methyl, an isopropyl, a cyclopropyl, a piperidin-4-yl or (R)tetrahydrofuran-3-yl;
or R₁ and R₂ together with N form an unsubstituted or substituted morpholinyl, piperazinyl, thiomorpholinyl, piperidinyl or pyrrolidinyl, wherein the substituent is a methyl on N;
R₃ is a hydrogen atom;
R₄ is a fluorine atom;
X is CH, CF or N; and
Y is CH, CF or N.

4. The compound or the pharmacologically or physiologically acceptable salt thereof according to claim 1, wherein the compound is shown as follows:

| No. | structural formula | R₁ | R₂ | X | Y | R₃ | R₄ |
|---|---|---|---|---|---|---|---|
| 5a | 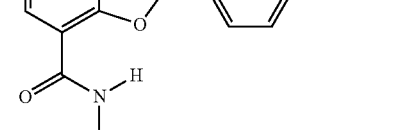 | CH₃ | CH₃ | CH | CH | H | F |
| 5b | 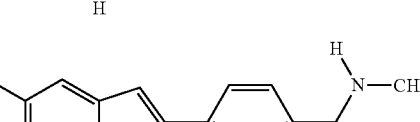 | CH₃ | CH₃ | CH | CH | H | F |
| 7a | 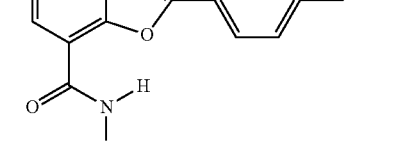 | CH₃ | CH₃ | CH | CH | Cl | F |
| 5c | 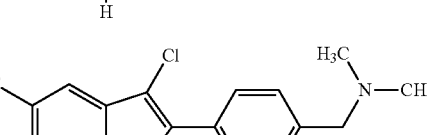 | H | CH₃ | CH | N | H | F |
| 5d | 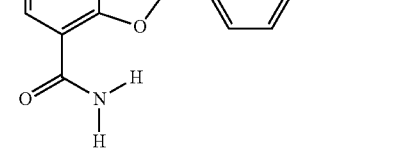 | H | CH₃ | N | CH | H | F |

| No. | structural formula | R₁ | R₂ | X | Y | R₃ | R₄ |
|-----|--------------------|----|----|---|---|----|----|
| 5e | | H | CH₃ | CH | CF | H | F |
| 5f | | \multicolumn{2}{l|}{$\underset{/}{R_1}{N-R_2}$ = N-pyrrolidinyl (N-methyl)} | CH | CH | H | F |
| 5g | | \multicolumn{2}{l|}{$\underset{/}{R_1}{N-R_2}$ = 4-methylpiperazinyl} | CH | CH | H | F |
| 5h | | \multicolumn{2}{l|}{$\underset{/}{R_1}{N-R_2}$ = piperidinyl} | CH | CH | H | F |
| 5j | | \multicolumn{2}{l|}{$\underset{/}{R_1}{N-R_2}$ = morpholinyl} | CH | CH | H | F |
| 5k | | \multicolumn{2}{l|}{$\underset{/}{R_1}{N-R_2}$ = thiomorpholinyl} | CH | CH | H | F |
| 5l | | H | 4-piperidinyl | CH | CH | H | F |

| No. | structural formula | R₁ | R₂ | X | Y | R₃ | R₄ |
|---|---|---|---|---|---|---|---|
| 5m | (structure: 5-fluoro-benzofuran-7-carboxamide with 4-((tetrahydrofuran-3-ylamino)methyl)phenyl) | H | (tetrahydrofuran-3-yl) | CH | CH | H | F |
| 5n | (structure: 5-fluoro-benzofuran-7-carboxamide with 4-((cyclopropylamino)methyl)phenyl) | H | (cyclopropyl) | CH | CH | H | F |
| 5o | (structure: 5-fluoro-benzofuran-7-carboxamide with 4-((isopropylamino)methyl)phenyl) | H | (isopropyl, H₃C–CH–CH₃) | CH | CH | H | F |
| 5p | (structure: 5-fluoro-benzofuran-7-carboxamide with 2-fluoro-4-((N-methylamino)methyl)phenyl) | H | CH₃ | CF | CH | H | F. |

5. The compound or the pharmacologically or physiologically acceptable salt thereof according to claim 1, wherein the pharmacologically or physiologically acceptable salt is a hydrochloride.

6. A method for the preparation of the compound according to claim 1, wherein, the synthesis route of the method is shown as scheme 1:

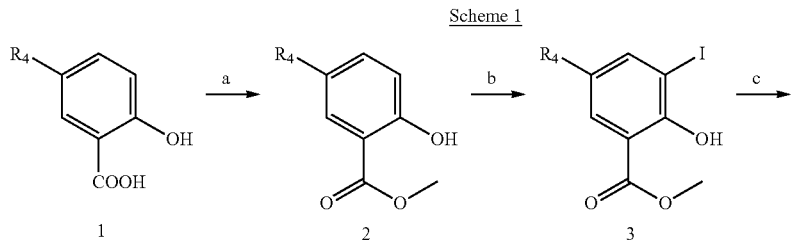

Scheme 1

-continued

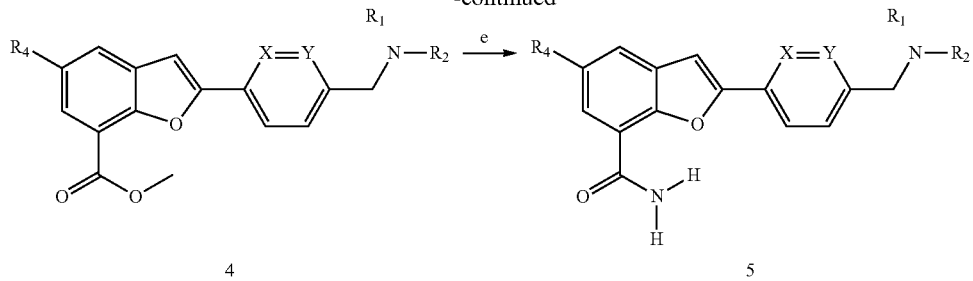

4 → 5

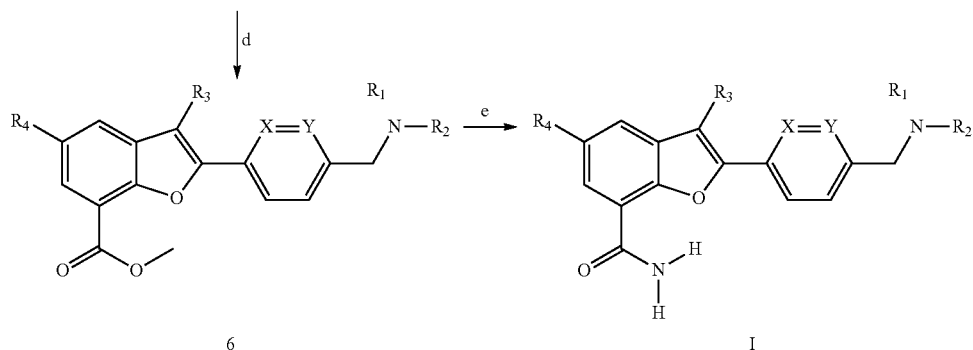

6 → I a) esterifying a substituted salicylic acid substituted on 5-position to form compound 2;
b) reacting compound 2 under iodination reaction conditions to form compound 3;
c) subjecting compound 3 and a substituted aromatic alkyne 8 to Sonogashira reaction conditions and then cyclization conditions to form compound 4;
d) optionally halogenating compound 4 to form compound 6;
e) subjecting compound 4 or 6 to ammonolysis reaction conditions to form compound 5 or I, respectively;
wherein the structural formula of the substituted aromatic alkyne 8 is as follows:

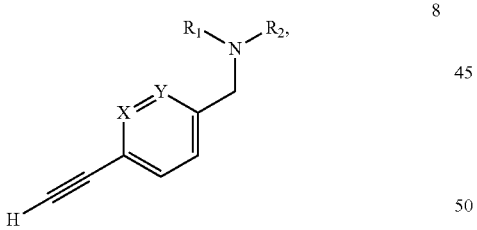

wherein, the definition of $R_1$, $R_2$, $R_3$, $R_4$, X or Y is described in claim 1.

7. A method for treating a PARP-related disease selected from the group consisting of ovarian cancer, stroke, myocardial infarction, lung cancer, breast cancer and prostate cancer comprising a step of administrating a compound or a pharmacologically or physiologically acceptable salt thereof according to claim 1 to a subject in need thereof.

8. The compound or the pharmacologically or physiologically acceptable salt thereof according to claim 1, wherein $R_4$ is a fluorine atom.

* * * * *